United States Patent [19]

Iwanaga et al.

[11] Patent Number: 5,795,962
[45] Date of Patent: Aug. 18, 1998

[54] HORSESHOE CRAB AMEBOCYTE LYSATE FACTOR G SUBUNIT A

[75] Inventors: Sadaaki Iwanaga; Tatsushi Muta; Noriaki Seki, all of Fukuoka; Toshio Oda, Higashiyamato, all of Japan

[73] Assignee: Seikagaku Kogyo Kabushiki Kaisha, Japan

[21] Appl. No.: 392,828

[22] PCT Filed: Jun. 29, 1994

[86] PCT No.: PCT/JP94/01057

§ 371 Date: Feb. 28, 1995

§ 102(e) Date: Feb. 28, 1995

[87] PCT Pub. No.: WO95/01432

PCT Pub. Date: Jan. 12, 1995

[30] Foreign Application Priority Data

Jun. 29, 1993 [JP] Japan .................................. 5-184403

[51] Int. Cl.$^6$ ...................... C07K 14/435; C07K 14/745; C12N 9/50
[52] U.S. Cl. ........................................... 530/350; 435/226
[58] Field of Search ........................ 435/219, 226; 530/350, 324

[56] References Cited

U.S. PATENT DOCUMENTS

| | | | |
|---|---|---|---|
| 4,107,077 | 8/1978 | Sullivan, Jr. et al. | 435/18 |
| 4,188,264 | 2/1980 | Iwanaga et al. | 435/18 |
| 4,495,294 | 1/1985 | Nakahara et al. | 435/18 |
| 5,047,353 | 9/1991 | Tsuchiya et al. | 45/18 |
| 5,155,032 | 10/1992 | Tanaka et al. | 435/184 |
| 5,179,006 | 1/1993 | Matuura et al. | 435/23 |
| 5,316,911 | 5/1994 | Baek et al. | 435/7.9 |
| 5,318,893 | 6/1994 | Matuura et al. | 435/23 |
| 5,389,547 | 2/1995 | Tanaka et al. | 436/94 |

FOREIGN PATENT DOCUMENTS

| | | |
|---|---|---|
| 0 370 700 | 5/1990 | European Pat. Off. . |
| 0 549 102 A1 | 6/1993 | European Pat. Off. . |
| 0 569 033 A2 | 11/1993 | European Pat. Off. . |

OTHER PUBLICATIONS

Noriaki Seki et al., "Horseshoe Crab (1,3)–β–D–Glucan–Sensitive Coagulation Factor G", *The Journal of Biological Chemistry*, 269, No. 2:1370–1374 (1994).

Sadaaki Iwanaga et al., "Role of Hemocyte–Derived Granular Components in Invertebrate Defense", *Annals of the New York Academy of Sciences*, 712:102–116 (1994).

Kenneth Soderhall et al., "The Effects of β1,3–Glucans on Blood Coagulation and Amebocyte Release in the Horseshoe Crab, *Limulus Polyphemus*", *Biol. Bull.* 169:661–674 (1985).

Tatsushi Muta et al., "Purified Horseshoe Crab Factor G", *The Journal of Biological Chemistry*, 270, No. 2:892–897 (1995).

Yoshiki Miura et al., "A Limulus Intracellular Coagulation Inhibitor with Characteristics of the Serpin Superfamily", *The Journal of Biological Chemistry*, 269, No. 1:542–547 (1994).

Gui–Hang Zhang et al., "Sensitive Quantitation of Endotoxin by Enzyme–Linked Immunosorbent Assay with Monoclonal Antibody against Limulus Peptide C", *Journal of Clinical Microbiology*, 416–422 (1994).

Sadakki Iwanaga, "The Limulus Clotting Reaction", *Current Opinion in Immunology*, 5:74–82 (1993).

Shigenori Tanaka et al., "Inhibition of High–Molecular–Weight–(1→3)–β–D–Glucan–Dependent Activation of a Limulus Coagulation Factor G by Laminaran Oligosaccharides and Curdlan Degradation Products", *Carbohydrate Research*, 244:115–127 (1993).

Shigenori Tanaka et al., "Activation of a Limulus Coagulation Factor G by (1→3)–β–D–Glucans", *Carbohydrate Research*, 218:167–174 (1991).

David S. Hodes et al., "Reaction of Fungal Products with Amebocyte Lysates of the Japanese Horseshoe Crab, *Tachypleus Tridentatus*", *Journal of Clinical Microbiology*, 1701–1704 (1987).

Obayashi et al., Clin. Chim. Acta 149:55–65, 1985.

Morita et al., FEBS Lett. 129(2):318–321, 1981.

Obayashi et al., J. Med. Vet. Mycol. 30:275–280, 1992.

*Primary Examiner*—Eric Grimes
*Attorney, Agent, or Firm*—Testa, Hurwitz & Thibeault, LLP

[57] ABSTRACT

This invention relates to a DNA shown by SEQ ID No. 1 and an amino acid sequence coded by said DNA. This invention also relates to a DNA and an amino acid sequence of subunit a of (1→3)-β-D-glucan sensitive factor derived from amebocytes of horseshoe crab and have potent affinity to (1→3)-β-D-glucan in cell walls of fungi. Therefore, the invention is useful for the diagnosis of fungal diseases and as antimicrobial or eradicating agent of fungi in combination with an antifungal agent.

4 Claims, 4 Drawing Sheets

```
FGA   4    PKWQLVWSDEFTNG--ISSDWEFEMGNGLN------GWGNNELQ      39
BG1 A1 421  AGMNLIWQDEFNGTTLDTSKWNYETGYYLNNDPATWGNAELQ       464

FGA   40   --YYRRENAQVEGGKLVITAKREDY------DGFKYTSARLKT       74
BG1 A1 465  HYTNSTQNVYVQDGKLNIKAMNDSKSFPQDPNRYAQYSSGKINT     508

FGA   75   QFDKSWKYGKIEAKMAIPSFRGVWVMFWMSGDNTHYVRWPSSGE     118
BG1 A1 509  KDKLSLKYGRVDFRAKLPTGDGVWPALWMLPKDSVYGTWAASGE     552

FGA   119  IDFIEHRNT------NNEKVRGTIHWSTPDGARAHHNRESHTNG    156
BG1 A1 553  IDVMEARGRLPGSVSGTIHFGGQWPVNQSSGGDYHFP-EGQTFA    595

FGA   157  IDYHIYSVEWNSSIVKWFVNGHQYFEVKIQ------GGVNGKSA    194
BG1 A1 596  NDYHVYSVVWEEDNIKWYVDGKFFYKVTNQQWYSTAAPNNPNAP    639

FGA   195  FRNKVFVILNMAIGGNWPGFDVADEAFPA-KMYIDYVRVYQDA     236
BG1 A1 640  FDEPFYLIMNLAVGGNFDGGRTPNASDIPATMQVDYVRVYKEQ     682
```

FIG. 2

```
FGA  391  SKLIQAESY--FDSSKVQLEDTSDVGGGKNVKCDNE  424
FGA  529  SKLIQAESY--FSYSEVQLEDTLDVGGGKNVKCDKE  562
Xyn  298  NTRIEAEDYDGINSSSIEIIGVPPEGGR-GIGYITS  332
     Z

FGA  425  GAWMAYKDIDFPSSGNYRIEYRVASERAGGKLSLDL  460
FGA  563  GAWMAYKDIDFPSSGSYRVEYRVASERAGGKLSLDL  598
Xyn  333  GDYLVYKSIDFGN-GATSFKAKVANAN-TSNIELRL  366
     Z

FGA  461  NAG-SIVLGMLDVPSTGGWQKWTTISHTVNVDSGTY  495
FGA  599  NAG-SIVLGMLDIPSTGGLQKWTTISHIVNVDLGTY  633
Xyn  367  NGPNGTLIGTLSVKSTGDWNTYEEQTCSISKVTGIN  402
     Z

FGA  496  NLGIYVQRASWNINWIKITKIPEQSNLNQGRRN     528
FGA  634  NLGIYVQKASWNINWIRITKV                 654
Xyn  403  DL-YLVFKGPVNIDWTFGVESSSTGLGDLNGD      434
     Z
```

FIG. 3

```
FGA   R1 247 LDGYYFVQNRHSELYLDVTDASNEDGAFLQQWSYSGNENQQFDFEHL- 293
FGA   R2 294 ENNVYKITNKKSGKSLDVYNFGTENGVRIQQWSYGGARNQQFTVQSV- 340
FGA   R3 341 GDGYYKIIPRGSGKIVEVADFSKDAGGKIQQWSDNNQLSGQWKLIKS- 387 xln A R1 351 ADG-GQIKGVGSGRCLDVPDASTSDGTQLQLMDCHSGTNQQWAATDAG 397
xln A R2 398 ELRVY-----GDKCLDAAGTS--NGSKVQIYSCWGGDNQKWRLNS--- 435
xln A R3 436 -DG--SVVGVQSGLCLDAVGNGTANGTLIQLYTCSNGSNQRWTRT--- 477
```

FIG. 4

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
( A ) LENGTH: 2409 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 114..2075

( x i ) SEQUENCE DESCRIPTION: SEQ ID NO:1:

```
GTGGGGGGTT TAGTTGAAAC AGTAAATACG TTAACTGTTT AATCTTGTTA ATTGCAATGT        60

TGGTGTTGCT GTGTTGTGTT GTTTGCATG TTGGTGTTGC AAGAATTTGC TGT AGC         116
                                                            Ser
                                                            1

CAC GAA CCA AAG TGG CAG CTC GTC TGG TCG GAT GAA TTT ACC AAT GGA        164
His Glu Pro Lys Trp Gln Leu Val Trp Ser Asp Glu Phe Thr Asn Gly
         5               10                  15

ATA AGT TCT GAT TGG GAA TTT GAA ATG GGC AAT GGC CTC AAT GGT TGG        212
Ile Ser Ser Asp Trp Glu Phe Glu Met Gly Asn Gly Leu Asn Gly Trp
        20               25                  30

GGT AAT AAC GAA CTG CAA TAT TAT CGT CGT GAA AAT GCC CAA GTT GAG        260
Gly Asn Asn Glu Leu Gln Tyr Tyr Arg Arg Glu Asn Ala Gln Val Glu
    35               40                  45

GGA GGG AAA CTG GTA ATT ACT GCT AAA AGA GAA GAC TAT GAT GGC TTC        308
Gly Gly Lys Leu Val Ile Thr Ala Lys Arg Glu Asp Tyr Asp Gly Phe
50                   55                  60                  65

AAA TAC ACT TCT GCT AGG CTG AAA ACC CAG TTT GAT AAA TCT TGG AAG        356
Lys Tyr Thr Ser Ala Arg Leu Lys Thr Gln Phe Asp Lys Ser Trp Lys
                70                  75                  80

TAT GGT AAA ATT GAA GCC AAA ATG GCG ATT CCA TCA TTT CGG GGA GTC        404
Tyr Gly Lys Ile Glu Ala Lys Met Ala Ile Pro Ser Phe Arg Gly Val
            85                  90                  95
```

| | | | | | | | | | | | | | | | | |
|---|---|---|---|---|---|---|---|---|---|---|---|---|---|---|---|---|
| TGG | GTG | ATG | TTC | TGG | ATG | TCA | GGA | GAC | AAC | ACT | AAT | TAT | GTT | AGA | TGG | 452 |
| Trp | Val | Met | Phe | Trp | Met | Ser | Gly | Asp | Asn | Thr | Asn | Tyr | Val | Arg | Trp | |
| | | 100 | | | | 105 | | | | | 110 | | | | | |
| CCA | TCT | TCT | GGT | GAA | ATT | GAC | TTT | ATT | GAA | CAT | AGA | AAC | ACT | AAC | AAT | 500 |
| Pro | Ser | Ser | Gly | Glu | Ile | Asp | Phe | Ile | Glu | His | Arg | Asn | Thr | Asn | Asn | |
| | 115 | | | | 120 | | | | | 125 | | | | | | |
| GAA | AAA | GTC | AGA | GGA | ACT | ATT | CAC | TGG | TCC | ACT | CCT | GAC | GGT | GCT | CAT | 548 |
| Glu | Lys | Val | Arg | Gly | Thr | Ile | His | Trp | Ser | Thr | Pro | Asp | Gly | Ala | His | |
| 130 | | | | 135 | | | | | 140 | | | | | | 145 | |
| GCG | CAT | CAT | AAC | AGA | GAA | AGT | AAT | ACA | AAT | GGG | ATT | GAT | TAT | CAC | ATT | 596 |
| Ala | His | His | Asn | Arg | Glu | Ser | Asn | Thr | Asn | Gly | Ile | Asp | Tyr | His | Ile | |
| | | | | 150 | | | | | 155 | | | | | | 160 | |
| TAT | TCT | GTA | GAG | TGG | AAT | TCT | TCC | ATT | GTT | AAA | TGG | TTT | GTT | AAT | GGA | 644 |
| Tyr | Ser | Val | Glu | Trp | Asn | Ser | Ser | Ile | Val | Lys | Trp | Phe | Val | Asn | Gly | |
| | | | | 165 | | | | | 170 | | | | | 175 | | |
| AAT | CAA | TAC | TTT | GAA | GTG | AAA | ATT | CAG | GGA | GGA | GTA | AAT | GGG | AAA | AGT | 692 |
| Asn | Gln | Tyr | Phe | Glu | Val | Lys | Ile | Gln | Gly | Gly | Val | Asn | Gly | Lys | Ser | |
| | | | 180 | | | | | 185 | | | | | 190 | | | |
| GCA | TTT | CGT | AAC | AAA | GTT | TTC | GTT | ATT | TTA | AAC | ATG | GCG | ATT | GGT | GGA | 740 |
| Ala | Phe | Arg | Asn | Lys | Val | Phe | Val | Ile | Leu | Asn | Met | Ala | Ile | Gly | Gly | |
| | 195 | | | | | 200 | | | | | 205 | | | | | |
| AAC | TGG | CCA | GGA | TTC | GAT | GTT | GCT | GAC | GAG | GCT | TTC | CCT | GCT | AAA | ATG | 788 |
| Asn | Trp | Pro | Gly | Phe | Asp | Val | Ala | Asp | Glu | Ala | Phe | Pro | Ala | Lys | Met | |
| 210 | | | | | 215 | | | | | 220 | | | | | 225 | |
| TAC | ATT | GAT | TAT | GTC | CGT | GTA | TAC | CAG | GAT | GCC | AGT | ACA | TCT | TCT | CCT | 836 |
| Tyr | Ile | Asp | Tyr | Val | Arg | Val | Tyr | Gln | Asp | Ala | Ser | Thr | Ser | Ser | Pro | |
| | | | | 230 | | | | 235 | | | | | 240 | | | |
| GTT | GGG | GAT | ACC | TCT | TTA | GAT | GGT | TAC | TAT | TTT | GTC | CAA | AAC | AGG | CAC | 884 |
| Val | Gly | Asp | Thr | Ser | Leu | Asp | Gly | Tyr | Tyr | Phe | Val | Gln | Asn | Arg | His | |
| | | | 245 | | | | | 250 | | | | | 255 | | | |
| AGT | GAA | TTG | TAT | CTT | GAT | GTC | ACT | GAT | GCC | AGT | AAC | GAA | GAT | GGA | GCA | 932 |
| Ser | Glu | Leu | Tyr | Leu | Asp | Val | Thr | Asp | Ala | Ser | Asn | Glu | Asp | Gly | Ala | |
| | | 260 | | | | | 265 | | | | | 270 | | | | |
| TTT | CTG | CAA | CAA | TGG | TCT | TAT | AGT | GGT | AAT | GAG | AAC | CAA | CAG | TTT | GAT | 980 |
| Phe | Leu | Gln | Gln | Trp | Ser | Tyr | Ser | Gly | Asn | Glu | Asn | Gln | Gln | Phe | Asp | |
| | 275 | | | | | 280 | | | | | 285 | | | | | |
| TTT | GAG | CAT | CTC | GAA | AAT | AAT | GTT | TAT | AAA | ATT | ACT | AAT | AAA | AAA | AGT | 1028 |
| Phe | Glu | His | Leu | Glu | Asn | Asn | Val | Tyr | Lys | Ile | Thr | Asn | Lys | Lys | Ser | |
| 290 | | | | | 295 | | | | | 300 | | | | | 305 | |
| GGA | AAA | TCT | TTG | GAT | GTT | TAT | AAT | TTT | GGG | ACT | GAG | AAT | GGT | GTT | AGA | 1076 |
| Gly | Lys | Ser | Leu | Asp | Val | Tyr | Asn | Phe | Gly | Thr | Glu | Asn | Gly | Val | Arg | |
| | | | | 310 | | | | | 315 | | | | | 320 | | |
| ATC | CAA | CAG | TGG | TCA | TAT | GGA | GGG | GCT | CGC | AAT | CAG | CAG | TTT | ACT | GTA | 1124 |
| Ile | Gln | Gln | Trp | Ser | Tyr | Gly | Gly | Ala | Arg | Asn | Gln | Gln | Phe | Thr | Val | |
| | | | 325 | | | | | 330 | | | | | 335 | | | |
| CAA | AGT | GTT | GGT | GAT | GGT | TAT | TAT | AAG | ATT | ATT | CCA | CGC | GGC | AGT | GGA | 1172 |
| Gln | Ser | Val | Gly | Asp | Gly | Tyr | Tyr | Lys | Ile | Ile | Pro | Arg | Gly | Ser | Gly | |
| | | 340 | | | | | 345 | | | | | 350 | | | | |
| AAG | TTA | GTG | GAA | GTA | GCA | GAT | TTT | AGT | AAA | GAT | GCA | GGA | GGG | AAG | ATA | 1220 |
| Lys | Leu | Val | Glu | Val | Ala | Asp | Phe | Ser | Lys | Asp | Ala | Gly | Gly | Lys | Ile | |
| | 355 | | | | | 360 | | | | | 365 | | | | | |
| CAA | CAA | TGG | TCT | GAT | AAC | AAC | CAA | TTA | TCT | GGA | CAG | TGG | AAA | CTT | ATT | 1268 |
| Gln | Gln | Trp | Ser | Asp | Asn | Asn | Gln | Leu | Ser | Gly | Gln | Trp | Lys | Leu | Ile | |
| 370 | | | | | 375 | | | | | 380 | | | | | 385 | |
| AAA | AGT | AAA | AGT | TAT | TCT | AAA | TTA | ATT | CAG | GCA | GAA | AGT | TAT | TTT | GAT | 1316 |
| Lys | Ser | Lys | Ser | Tyr | Ser | Lys | Leu | Ile | Gln | Ala | Glu | Ser | Tyr | Phe | Asp | |
| | | | | 390 | | | | | 395 | | | | | 400 | | |
| TCC | TCA | AAA | GTA | CAA | TTG | GAA | GAT | ACC | TCA | GAT | GTA | GGA | GGT | GGG | AAG | 1364 |
| Ser | Ser | Lys | Val | Gln | Leu | Glu | Asp | Thr | Ser | Asp | Val | Gly | Gly | Gly | Lys | |
| | | | 405 | | | | | 410 | | | | | 415 | | | |

| | | | | | | | | | | | | | | | | |
|---|---|---|---|---|---|---|---|---|---|---|---|---|---|---|---|---|
| AAT | GTT | AAA | TGT | GAT | AAT | GAA | GGA | GCC | TGG | ATG | GCT | TAT | AAG | GAT | ATT | 1412 |
| Asn | Val | Lys | Cys | Asp | Asn | Glu | Gly | Ala | Trp | Met | Ala | Tyr | Lys | Asp | Ile | |
| | | 420 | | | | 425 | | | | | 430 | | | | | |
| GAT | TTC | CCC | AGT | TCA | GGT | AAT | TAT | CGA | ATA | GAA | TAC | AGA | GTA | GCA | AGT | 1460 |
| Asp | Phe | Pro | Ser | Ser | Gly | Asn | Tyr | Arg | Ile | Glu | Tyr | Arg | Val | Ala | Ser | |
| | 435 | | | | 440 | | | | | 445 | | | | | | |
| GAA | CGT | GCA | GGA | GGA | AAG | CTG | TCT | CTG | GAT | TTG | AAT | GCA | GGC | TCT | ATA | 1508 |
| Glu | Arg | Ala | Gly | Gly | Lys | Leu | Ser | Leu | Asp | Leu | Asn | Ala | Gly | Ser | Ile | |
| 450 | | | | 455 | | | | 460 | | | | | 465 | | | |
| GTT | CTT | GGC | ATG | CTG | GAT | GTT | CCT | TCA | ACA | GGA | GGA | TGG | CAG | AAG | TGG | 1556 |
| Val | Leu | Gly | Met | Leu | Asp | Val | Pro | Ser | Thr | Gly | Gly | Trp | Gln | Lys | Trp | |
| | | | | 470 | | | | 475 | | | | | 480 | | | |
| ACC | ACC | ATT | TCC | CAT | ACA | GTG | AAT | GTG | GAT | TCA | GGT | ACA | TAT | AAC | TTG | 1604 |
| Thr | Thr | Ile | Ser | His | Thr | Val | Asn | Val | Asp | Ser | Gly | Thr | Tyr | Asn | Leu | |
| | | | 485 | | | | | 490 | | | | | 495 | | | |
| GGG | ATC | TAT | GTT | CAA | CGA | GCC | AGC | TGG | AAT | ATC | AAC | TGG | ATA | AAG | ATT | 1652 |
| Gly | Ile | Tyr | Val | Gln | Arg | Ala | Ser | Trp | Asn | Ile | Asn | Trp | Ile | Lys | Ile | |
| | | 500 | | | | | 505 | | | | | 510 | | | | |
| ACA | AAA | ATA | CCT | GAA | CAG | TCA | AAT | TTG | AAT | CAA | GGG | CGT | CGT | AAT | TCT | 1700 |
| Thr | Lys | Ile | Pro | Glu | Gln | Ser | Asn | Leu | Asn | Gln | Gly | Arg | Arg | Asn | Ser | |
| | 515 | | | | | 520 | | | | | 525 | | | | | |
| AAA | TTA | ATT | CAG | GCA | GAA | AGT | TAT | TTT | AGT | TAC | TCA | GAA | GTA | CAA | CTG | 1748 |
| Lys | Leu | Ile | Gln | Ala | Glu | Ser | Tyr | Phe | Ser | Tyr | Ser | Glu | Val | Gln | Leu | |
| 530 | | | | | 535 | | | | | 540 | | | | | 545 | |
| GAA | GAT | ACC | TTA | GAT | GTA | GGA | GGT | GGA | AAG | AAT | GTT | AAA | TGT | GAT | AAA | 1796 |
| Glu | Asp | Thr | Leu | Asp | Val | Gly | Gly | Gly | Lys | Asn | Val | Lys | Cys | Asp | Lys | |
| | | | | 550 | | | | | 555 | | | | | 560 | | |
| GAA | GGG | GCC | TGG | ATG | GCT | TAC | AAG | GAT | ATT | GAT | TTC | CCC | AGT | TCA | GGA | 1844 |
| Glu | Gly | Ala | Trp | Met | Ala | Tyr | Lys | Asp | Ile | Asp | Phe | Pro | Ser | Ser | Gly | |
| | | | 565 | | | | | 570 | | | | | 575 | | | |
| AGT | TAT | CGA | GTA | GAA | TAC | AGA | GTG | GCA | AGT | GAA | CGT | GCA | GGA | GGA | AAG | 1892 |
| Ser | Tyr | Arg | Val | Glu | Tyr | Arg | Val | Ala | Ser | Glu | Arg | Ala | Gly | Gly | Lys | |
| | | 580 | | | | | 585 | | | | | 590 | | | | |
| CTG | TCC | CTA | GAT | TTG | AAT | GCA | GGC | TCT | ATA | GTG | CTT | GGC | ATG | CTG | GAT | 1940 |
| Leu | Ser | Leu | Asp | Leu | Asn | Ala | Gly | Ser | Ile | Val | Leu | Gly | Met | Leu | Asp | |
| | 595 | | | | | 600 | | | | | 605 | | | | | |
| ATT | CCT | TCA | ACA | GGA | GGA | TTG | CAG | AAG | TGG | ACC | ACC | ATT | TCT | CAT | ATA | 1988 |
| Ile | Pro | Ser | Thr | Gly | Gly | Leu | Gln | Lys | Trp | Thr | Thr | Ile | Ser | His | Ile | |
| 610 | | | | | 615 | | | | | 620 | | | | | 625 | |
| GTG | AAT | GTG | GAT | TTA | GGT | ACA | TAT | AAC | TTG | GGA | ATT | TAT | GTT | CAA | AAA | 2036 |
| Val | Asn | Val | Asp | Leu | Gly | Thr | Tyr | Asn | Leu | Gly | Ile | Tyr | Val | Gln | Lys | |
| | | | | 630 | | | | | 635 | | | | | 640 | | |
| GCC | AGT | TGG | AAT | ATC | AAT | TGG | ATT | AGA | ATT | ACA | AAA | GTG | TAGGATACAA | | | 2085 |
| Ala | Ser | Trp | Asn | Ile | Asn | Trp | Ile | Arg | Ile | Thr | Lys | Val | | | | |
| | | | 645 | | | | | 650 | | | | | | | | |

| | | | | |
|---|---|---|---|---|
| GAGCAAACCA | ATTGTATTAT | TTTGAAGAAA | CAACAGCTGT | TGACCATAAT | CTTTGTTCAT | 2145 |
| TGAGAATTTA | TCCAACTGTT | ATAGAATCTA | TCACCTTTCC | AGATGTAACG | CATTGCTGAT | 2205 |
| GGTTTTGAAC | TAATAAATGA | GGAGATTATA | AGTGCTAATG | TGTTTGTTAT | ATCTTTAATT | 2265 |
| TTTAAAAACA | AATTATCAAC | TAACTTTTCA | ATTCAGGCAT | GGTGTTTCTC | TTTTTAATCT | 2325 |
| GTATTTCTAA | TAAATTAATG | TCTTTAAGAG | TTGTTTTGTT | TACAATAAAT | AAAGTTTGAT | 2385 |
| TGTGTGGGAT | AAAAAAAAAA | AAAA | | | | 2409 |

( 2 ) INFORMATION FOR SEQ ID NO:2:

( i ) SEQUENCE CHARACTERISTICS:
        ( A ) LENGTH: 654 amino acids
        ( B ) TYPE: amino acid
        ( D ) TOPOLOGY: linear (ii) MOLECULE TYPE: protein (xi) SEQUENCE DESCRIPTION: SEQ ID NO:2:

```
Ser His Glu Pro Lys Trp Gln Leu Val Trp Ser Asp Glu Phe Thr Asn
 1               5                  10                  15
Gly Ile Ser Ser Asp Trp Glu Phe Glu Met Gly Asn Gly Leu Asn Gly
                 20                  25                  30
Trp Gly Asn Asn Glu Leu Gln Tyr Tyr Arg Arg Glu Asn Ala Gln Val
             35                  40                  45
Glu Gly Gly Lys Leu Val Ile Thr Ala Lys Arg Glu Asp Tyr Asp Gly
     50                  55                  60
Phe Lys Tyr Thr Ser Ala Arg Leu Lys Thr Gln Phe Asp Lys Ser Trp
 65                  70                  75                  80
Lys Tyr Gly Lys Ile Glu Ala Lys Met Ala Ile Pro Ser Phe Arg Gly
                 85                  90                  95
Val Trp Val Met Phe Trp Met Ser Gly Asp Asn Thr Asn Tyr Val Arg
                100                 105                 110
Trp Pro Ser Ser Gly Glu Ile Asp Phe Ile Glu His Arg Asn Thr Asn
             115                 120                 125
Asn Glu Lys Val Arg Gly Thr Ile His Trp Ser Thr Pro Asp Gly Ala
    130                 135                 140
His Ala His His Asn Arg Glu Ser Asn Thr Asn Gly Ile Asp Tyr His
145                 150                 155                 160
Ile Tyr Ser Val Glu Trp Asn Ser Ser Ile Val Lys Trp Phe Val Asn
                165                 170                 175
Gly Asn Gln Tyr Phe Glu Val Lys Ile Gln Gly Gly Val Asn Gly Lys
            180                 185                 190
Ser Ala Phe Arg Asn Lys Val Phe Val Ile Leu Asn Met Ala Ile Gly
        195                 200                 205
Gly Asn Trp Pro Gly Phe Asp Val Ala Asp Glu Ala Phe Pro Ala Lys
    210                 215                 220
Met Tyr Ile Asp Tyr Val Arg Val Tyr Gln Asp Ala Ser Thr Ser Ser
225                 230                 235                 240
Pro Val Gly Asp Thr Ser Leu Asp Gly Tyr Tyr Phe Val Gln Asn Arg
                245                 250                 255
His Ser Glu Leu Tyr Leu Asp Val Thr Asp Ala Ser Asn Glu Asp Gly
            260                 265                 270
Ala Phe Leu Gln Gln Trp Ser Tyr Ser Gly Asn Glu Asn Gln Gln Phe
        275                 280                 285
Asp Phe Glu His Leu Glu Asn Asn Val Tyr Lys Ile Thr Asn Lys Lys
    290                 295                 300
Ser Gly Lys Ser Leu Asp Val Tyr Asn Phe Gly Thr Glu Asn Gly Val
305                 310                 315                 320
Arg Ile Gln Gln Trp Ser Tyr Gly Gly Ala Arg Asn Gln Gln Phe Thr
                325                 330                 335
Val Gln Ser Val Gly Asp Gly Tyr Tyr Lys Ile Ile Pro Arg Gly Ser
            340                 345                 350
Gly Lys Leu Val Glu Val Ala Asp Phe Ser Lys Asp Ala Gly Gly Lys
        355                 360                 365
Ile Gln Gln Trp Ser Asp Asn Asn Gln Leu Ser Gly Gln Trp Lys Leu
    370                 375                 380
Ile Lys Ser Lys Ser Tyr Ser Lys Leu Ile Gln Ala Glu Ser Tyr Phe
385                 390                 395                 400
Asp Ser Ser Lys Val Gln Leu Glu Asp Thr Ser Asp Val Gly Gly Gly
```

|   |   |   |   |   |   |   |   |   |   |   |   |   |   |
|---|---|---|---|---|---|---|---|---|---|---|---|---|---|
|   |   |   |   | 405 |   |   |   | 410 |   |   |   | 415 |   |
| Lys | Asn | Val | Lys | Cys | Asp | Asn | Glu | Gly | Ala | Trp | Met | Ala | Tyr | Lys | Asp |
|   |   |   | 420 |   |   |   |   | 425 |   |   |   |   | 430 |
| Ile | Asp | Phe | Pro | Ser | Ser | Gly | Asn | Tyr | Arg | Ile | Glu | Tyr | Arg | Val | Ala |
|   |   | 435 |   |   |   |   | 440 |   |   |   |   | 445 |
| Ser | Glu | Arg | Ala | Gly | Gly | Lys | Leu | Ser | Leu | Asp | Leu | Asn | Ala | Gly | Ser |
|   | 450 |   |   |   |   | 455 |   |   |   |   | 460 |
| Ile | Val | Leu | Gly | Met | Leu | Asp | Val | Pro | Ser | Thr | Gly | Gly | Trp | Gln | Lys |
| 465 |   |   |   |   | 470 |   |   |   |   | 475 |   |   |   |   | 480 |
| Trp | Thr | Thr | Ile | Ser | His | Thr | Val | Asn | Val | Asp | Ser | Gly | Thr | Tyr | Asn |
|   |   |   |   | 485 |   |   |   |   | 490 |   |   |   |   | 495 |
| Leu | Gly | Ile | Tyr | Val | Gln | Arg | Ala | Ser | Trp | Asn | Ile | Asn | Trp | Ile | Lys |
|   |   |   | 500 |   |   |   |   | 505 |   |   |   |   | 510 |
| Ile | Thr | Lys | Ile | Pro | Glu | Gln | Ser | Asn | Leu | Asn | Gln | Gly | Arg | Arg | Asn |
|   |   | 515 |   |   |   |   | 520 |   |   |   |   | 525 |
| Ser | Lys | Leu | Ile | Gln | Ala | Glu | Ser | Tyr | Phe | Ser | Tyr | Ser | Glu | Val | Gln |
|   | 530 |   |   |   |   | 535 |   |   |   |   | 540 |
| Leu | Glu | Asp | Thr | Leu | Asp | Val | Gly | Gly | Gly | Lys | Asn | Val | Lys | Cys | Asp |
| 545 |   |   |   |   | 550 |   |   |   |   | 555 |   |   |   |   | 560 |
| Lys | Glu | Gly | Ala | Trp | Met | Ala | Tyr | Lys | Asp | Ile | Asp | Phe | Pro | Ser | Ser |
|   |   |   |   | 565 |   |   |   |   | 570 |   |   |   |   | 575 |
| Gly | Ser | Tyr | Arg | Val | Glu | Tyr | Arg | Val | Ala | Ser | Glu | Arg | Ala | Gly | Gly |
|   |   |   | 580 |   |   |   |   | 585 |   |   |   |   | 590 |
| Lys | Leu | Ser | Leu | Asp | Leu | Asn | Ala | Gly | Ser | Ile | Val | Leu | Gly | Met | Leu |
|   |   |   | 595 |   |   |   |   | 600 |   |   |   |   | 605 |
| Asp | Ile | Pro | Ser | Thr | Gly | Gly | Leu | Gln | Lys | Trp | Thr | Thr | Ile | Ser | His |
|   |   | 610 |   |   |   |   | 615 |   |   |   |   | 620 |
| Ile | Val | Asn | Val | Asp | Leu | Gly | Thr | Tyr | Asn | Leu | Gly | Ile | Tyr | Val | Gln |
| 625 |   |   |   |   | 630 |   |   |   |   | 635 |   |   |   |   | 640 |
| Lys | Ala | Ser | Trp | Asn | Ile | Asn | Trp | Ile | Arg | Ile | Thr | Lys | Val |
|   |   |   |   | 645 |   |   |   |   | 650 |

( 2 ) INFORMATION FOR SEQ ID NO:3:

( i ) SEQUENCE CHARACTERISTICS:
        ( A ) LENGTH: 1979 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 194..1027

( x i ) SEQUENCE DESCRIPTION: SEQ ID NO:3:

```
GAAGACAAGA GAGTTGAAAC AACCATAGCC TGTTTGCTTA TGACTTTCAA TAAGAGATAC        60

TCGGCTTAAA GGGAACTGAC TTATTCGTAG AGGCTATACC ATGGATATCA GTTTCCTGGT       120

TTTTATCACA CTGTCTATGG CTCTCTTCTC GAGCAACGTG ACAGGAACGT CAGTAACATC       180

AAGGGTACGA CGT GGA ATA AAT GAA AAA CAT TGT GGG TTC CGA CCA GTA         229
            Gly Ile Asn Glu Lys His Cys Gly Phe Arg Pro Val
             1               5                  10

ATT ACA AGA ATT ATT GGT GGA GGA ATA GCG ACG CCT CAT TCA TGG CCG         277
Ile Thr Arg Ile Ile Gly Gly Gly Ile Ala Thr Pro His Ser Trp Pro
         15                  20                  25

TGG ATG GTT GGA ATT TTC AAA GTA AAT CCT CAC CGT TTC CTT TGT GGT         325
Trp Met Val Gly Ile Phe Lys Val Asn Pro His Arg Phe Leu Cys Gly
```

```
                30                          35                          40
GGA  TCT  ATT  ATT  AAT  AAA  GTC  TCT  GTT  GTT  ACT  GCC  GCC  CAT  TGT  CTT        373
Gly  Ser  Ile  Ile  Asn  Lys  Val  Ser  Val  Val  Thr  Ala  Ala  His  Cys  Leu
 45                      50                          55                      60

GTG  ACG  CAG  TTT  GGA  AAC  AGA  CAG  AAT  TAT  TCT  ATC  TTC  GTA  AGA  GTT        421
Val  Thr  Gln  Phe  Gly  Asn  Arg  Gln  Asn  Tyr  Ser  Ile  Phe  Val  Arg  Val
                         65                          70                      75

GGA  GCC  CAT  GAC  ATA  GAC  AAT  TCG  GGT  ACA  AAT  TAT  CAA  GTG  GAT  AAA        469
Gly  Ala  His  Asp  Ile  Asp  Asn  Ser  Gly  Thr  Asn  Tyr  Gln  Val  Asp  Lys
                    80                          85                      90

GTT  ATT  GTT  CAC  CAG  GGC  TAC  AAA  CAC  CAT  TCA  CAC  TAC  TAC  GAT  ATC        517
Val  Ile  Val  His  Gln  Gly  Tyr  Lys  His  His  Ser  His  Tyr  Tyr  Asp  Ile
               95                         100                         105

GGT  TTG  ATT  TTA  CTC  TCG  AAA  CCA  GTC  GAA  TAC  AAC  GAC  AAA  ATA  CAG        565
Gly  Leu  Ile  Leu  Leu  Ser  Lys  Pro  Val  Glu  Tyr  Asn  Asp  Lys  Ile  Gln
110                           115                         120

CCT  GTC  TGT  ATT  CCT  GAG  TTC  AAC  AAA  CCT  CAC  GTG  AAC  TTG  AAC  AAT        613
Pro  Val  Cys  Ile  Pro  Glu  Phe  Asn  Lys  Pro  His  Val  Asn  Leu  Asn  Asn
125                      130                         135                     140

ATT  AAG  GTC  GTC  ATT  ACT  GGT  TGG  GGT  GTT  ACT  GGG  AAA  GCT  ACT  GAG        661
Ile  Lys  Val  Val  Ile  Thr  Gly  Trp  Gly  Val  Thr  Gly  Lys  Ala  Thr  Glu
                         145                         150                     155

AAA  CGT  AAC  GTT  CTT  CGT  GAA  TTG  GAG  TTG  CCC  GTG  GTT  ACA  AAC  GAA        709
Lys  Arg  Asn  Val  Leu  Arg  Glu  Leu  Glu  Leu  Pro  Val  Val  Thr  Asn  Glu
                    160                         165                     170

CAG  TGC  AAC  AAA  TCT  TAT  CAG  ACA  CTC  CCA  TTC  TCA  AAA  TTG  AAC  CGA        757
Gln  Cys  Asn  Lys  Ser  Tyr  Gln  Thr  Leu  Pro  Phe  Ser  Lys  Leu  Asn  Arg
               175                         180                    185

GGA  ATC  ACT  AAC  GAC  ATG  ATT  TGT  GCG  GGG  TTT  CCG  GAA  GGA  GGG  AAA        805
Gly  Ile  Thr  Asn  Asp  Met  Ile  Cys  Ala  Gly  Phe  Pro  Glu  Gly  Gly  Lys
     190                         195                         200

GAT  GCT  TGT  CAG  GGC  GAC  TCT  GGT  GGT  CCC  CTG  ATG  TAT  CAG  AAT  CCA        853
Asp  Ala  Cys  Gln  Gly  Asp  Ser  Gly  Gly  Pro  Leu  Met  Tyr  Gln  Asn  Pro
205                           210                         215                220

ACA  ACA  GGA  AGA  GTG  AAA  ATA  GTT  GGA  GTT  GTA  TCA  TTT  GGG  TTC  GAA        901
Thr  Thr  Gly  Arg  Val  Lys  Ile  Val  Gly  Val  Val  Ser  Phe  Gly  Phe  Glu
                    225                         230                    235

TGT  GCT  CGT  CCC  AAC  TTC  CCC  GGT  GTT  TAC  ACG  CGC  CTC  TCG  AGC  TAC        949
Cys  Ala  Arg  Pro  Asn  Phe  Pro  Gly  Val  Tyr  Thr  Arg  Leu  Ser  Ser  Tyr
               240                         245                    250

GTT  AAC  TGG  CTC  CAG  GAA  ATC  ACC  TTC  GGA  CAG  TCA  CTC  GCT  TCT  TTA        997
Val  Asn  Trp  Leu  Gln  Glu  Ile  Thr  Phe  Gly  Gln  Ser  Leu  Ala  Ser  Leu
          255                         260                    265

TTT  GAA  GTT  GTA  CCA  ATA  TTT  ATA  CCC  GAG  TGAGACTGAA  GATAAATATT              1047
Phe  Glu  Val  Val  Pro  Ile  Phe  Ile  Pro  Glu
270                           275

GAAGAGAAAT  CTAGAATAAT  GTACAATATA  AGAAGCCTGA  AATTACTGAA  ATAGAAAGGC                1107

GCGTGATGAG  AAATACGTTT  CAAATTTTAT  TTTTTATTAA  CTTTATTGTG  TTTAACTATT                1167

CTTTACGTGG  GACATGAAAT  ATAAATCTTT  ATTTCTTCTT  TATATACTTT  AGATTTTCAT                1227

TTCATCTATC  TTTATCAGTT  TTGTAATGTT  ACTAATAATA  TTTCTTATGG  CACGGATCGA                1287

GCCTCGTGAA  TCACAGTAAA  TAATAATAAT  TATAAAATCA  CACATTATTA  AAAGCAATAG                1347

CATTCAGAGT  GAGTAACATA  TAAACTTCAC  TATGAGTGGA  CTTTTTATT   CACATTTTAA                1407

GTTCATTACT  AACTGTTGGG  AGGTCTTTAT  ATTGTTGTAT  ATTTATATAT  TAATTAGGTT                1467

GGTTTAGTAC  ATTGTTGTTA  ATGGTGGAAT  AGGGCGTAGG  TTTTAAATGT  GTTTGCAAAA                1527

AAACAAACAA  AACAAGTAAT  GGTGGATGAT  GGTTCCAAAG  TAACCGAAAG  AACACTTTGA                1587
```

-continued

```
ACATTTTTAT ACAAAAATTT ATGTTTTAAA ATACGAGTAT ATACAATCGA TCTCTAAGTA    1647
CAAGAAAAAC TGAAGTGTTC ATTCAGGTTT AACAGTGCAA CTTAAATCAA CAGTTAGTTG    1707
TTCACTAAAC ATTACAATTT GATCCTTTAT AAACGCTAAT ACTGTTAAA  CAGTCAGTAA    1767
TAATACAGTA TCATAGCATA TCATATATGA AGGTATTTTA ACATTCTATA TACAAAGCCA    1827
GAATTGAAAA CGGTAATATT TTGTACGATT AGTGAATTAT TGTTTTAAG  AACAAACTGG    1887
TATCAAATTT AAAATATGAA TCTGTGATTT AATATTTTTT ACAACGTTCT AACTTACCAC    1947
TTTTGTTGTG AATAAAGGTG TTTACAAATG GA                                  1979
```

( 2 ) INFORMATION FOR SEQ ID NO:4:

( i ) SEQUENCE CHARACTERISTICS:
    ( A ) LENGTH: 278 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Gly Ile Asn Glu Lys His Cys Gly Phe Arg Pro Val Ile Thr Arg Ile
  1               5                  10                  15
Ile Gly Gly Gly Ile Ala Thr Pro His Ser Trp Pro Trp Met Val Gly
             20                  25                  30
Ile Phe Lys Val Asn Pro His Arg Phe Leu Cys Gly Gly Ser Ile Ile
         35                  40                  45
Asn Lys Val Ser Val Val Thr Ala Ala His Cys Leu Val Thr Gln Phe
     50                  55                  60
Gly Asn Arg Gln Asn Tyr Ser Ile Phe Val Arg Val Gly Ala His Asp
 65                  70                  75                  80
Ile Asp Asn Ser Gly Thr Asn Tyr Gln Val Asp Lys Val Ile Val His
                 85                  90                  95
Gln Gly Tyr Lys His His Ser His Tyr Tyr Asp Ile Gly Leu Ile Leu
            100                 105                 110
Leu Ser Lys Pro Val Glu Tyr Asn Asp Lys Ile Gln Pro Val Cys Ile
        115                 120                 125
Pro Glu Phe Asn Lys Pro His Val Asn Leu Asn Asn Ile Lys Val Val
    130                 135                 140
Ile Thr Gly Trp Gly Val Thr Gly Lys Ala Thr Glu Lys Arg Asn Val
145                 150                 155                 160
Leu Arg Glu Leu Glu Leu Pro Val Val Thr Asn Glu Gln Cys Asn Lys
                165                 170                 175
Ser Tyr Gln Thr Leu Pro Phe Ser Lys Leu Asn Arg Gly Ile Thr Asn
            180                 185                 190
Asp Met Ile Cys Ala Gly Phe Pro Glu Gly Gly Lys Asp Ala Cys Gln
        195                 200                 205
Gly Asp Ser Gly Gly Pro Leu Met Tyr Gln Asn Pro Thr Thr Gly Arg
    210                 215                 220
Val Lys Ile Val Gly Val Val Ser Phe Gly Phe Glu Cys Ala Arg Pro
225                 230                 235                 240
Asn Phe Pro Gly Val Tyr Thr Arg Leu Ser Ser Tyr Val Asn Trp Leu
                245                 250                 255
Gln Glu Ile Thr Phe Gly Gln Ser Leu Ala Ser Leu Phe Glu Val Val
            260                 265                 270
Pro Ile Phe Ile Pro Glu
        275
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /note= "TABLE 1, PEPTIDE 1"

( x i ) SEQUENCE DESCRIPTION: SEQ ID NO:5:

Ser Xaa Glu Pro Lys Xaa Gln Leu Val
1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /note= "TABLE 1, PEPTIDE 2"

( x i ) SEQUENCE DESCRIPTION: SEQ ID NO:6:

Arg Glu Asp Tyr Asp Gly Phe Lys
1               5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /note= "TABLE 1, PEPTIDE 3"

( x i ) SEQUENCE DESCRIPTION: SEQ ID NO:7:

Tyr Thr Ser Ala Arg Leu Lys
1               5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "TABLE 1, PEPTIDE 4"

( x i ) SEQUENCE DESCRIPTION: SEQ ID NO:8:

```
        Thr  Gln  Phe  Asp  Lys
        1                   5
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..26
        ( D ) OTHER INFORMATION: /note= "TABLE 1, PEPTIDE 7"

( x i ) SEQUENCE DESCRIPTION: SEQ ID NO:9:

```
Met  Ala  Ile  Pro  Ser  Phe  Arg  Gly  Val  Trp  Val  Met  Phe  Trp  Met  Ser
1                   5                        10                       15

Gly  Xaa  Asn  Thr  Asn  Tyr  Val  Xaa  Xaa  Pro
                    20                   25
```

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note= "TABLE 1, PEPTIDE 8"

( x i ) SEQUENCE DESCRIPTION: SEQ ID NO:10:

```
Ser  Ala  Phe  Arg  Asn  Lys
1                   5
```

( 2 ) INFORMATION FOR SEQ ID NO:11:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note= "TABLE 1, PEPTIDE 9"

( x i ) SEQUENCE DESCRIPTION: SEQ ID NO:11:

```
Val  Phe  Val  Ile  Leu  Asn  Met  Ala  Ile  Gly  Gly  Asn  Xaa  Pro  Gly  Phe
1                   5                        10                       15

Xaa  Val  Ala
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /note= "TABLE 1, PEPTIDE 10"

( x i ) SEQUENCE DESCRIPTION: SEQ ID NO:12:

```
Ile Ile Pro Arg Gly Ser Gly Lys
1               5
```

( 2 ) INFORMATION FOR SEQ ID NO:13:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..13
    ( D ) OTHER INFORMATION: /note= "TABLE 1, PEPTIDE 11"

( x i ) SEQUENCE DESCRIPTION: SEQ ID NO:13:

```
Val Gln Leu Glu Asp Thr Ser Asp Val Gly Gly Gly Lys
1               5                   10
```

( 2 ) INFORMATION FOR SEQ ID NO:14:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..11
    ( D ) OTHER INFORMATION: /note= "TABLE 1, PEPTIDE 12"

( x i ) SEQUENCE DESCRIPTION: SEQ ID NO:14:

```
Cys Asp Asn Glu Gly Ala Trp Met Ala Tyr Lys
1               5                   10
```

( 2 ) INFORMATION FOR SEQ ID NO:15:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..17
    ( D ) OTHER INFORMATION: /note= "TABLE 1, PEPTIDE 13"

( x i ) SEQUENCE DESCRIPTION: SEQ ID NO:15:

```
Asp Ile Asp Phe Pro Ser Ser Gly Asn Tyr Xaa Ile Glu Tyr Xaa Val
1               5                   10                  15
Ala
```

( 2 ) INFORMATION FOR SEQ ID NO:16:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..16
    ( D ) OTHER INFORMATION: /note= "TABLE 1, PEPTIDE 14"

( x i ) SEQUENCE DESCRIPTION: SEQ ID NO:16:

```
Leu  Ile  Gln  Ala  Glu  Xaa  Tyr  Phe  Xaa  Tyr  Xaa  Glu  Val  Gln  Leu  Glu
1                   5                        10                       15
```

( 2 ) INFORMATION FOR SEQ ID NO:17:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /note= "TABLE 1, PEPTIDE 15"

( x i ) SEQUENCE DESCRIPTION: SEQ ID NO:17:

```
Glu  Gly  Ala  Trp  Met  Ala  Tyr  Lys
1                   5
```

( 2 ) INFORMATION FOR SEQ ID NO:18:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..19
    ( D ) OTHER INFORMATION: /note= "TABLE 1, PEPTIDE 16"

( x i ) SEQUENCE DESCRIPTION: SEQ ID NO:18:

```
Val  Arg  Gly  Thr  Ile  His  Trp  Ser  Thr  Pro  Asp  Gly  Ala  His  Ala  His
1                   5                        10                       15

His  Asn  Arg
```

( 2 ) INFORMATION FOR SEQ ID NO:19:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..25
    ( D ) OTHER INFORMATION: /product="DNA SEQUENCE A'"

( x i ) SEQUENCE DESCRIPTION: SEQ ID NO:19:

CGGAGCTCGA RGAYTAYGAY GGNTT                                                25

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..26
        ( D ) OTHER INFORMATION: /product="DNA SEQUENCE B'"

( x i ) SEQUENCE DESCRIPTION: SEQ ID NO:20:

CGGAATTCCA TCCARAACAT NACCCA                                               26

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /product="DNA SEQUENCE SECTION 8
            OF SPECIFICATION"

( x i ) SEQUENCE DESCRIPTION: SEQ ID NO:21:

AGCCACGAAC CAAAGTGGCA                                                      20

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..24
        ( D ) OTHER INFORMATION: /product="DNA PROBE SECTION 8 OF
            SPECIFICATION"

( x i ) SEQUENCE DESCRIPTION: SEQ ID NO:22:

AAACAGACCA TGAGCCACGA ACCA                                                 24

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "TABLE 2, PEPTIDE 1"

( x i ) SEQUENCE DESCRIPTION: SEQ ID NO:23:

Gly Ile Asn Glu Lys
1               5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /note= "TABLE 2, PEPTIDE 2"

( x i ) SEQUENCE DESCRIPTION: SEQ ID NO:24:

Xaa Xaa Gly Phe Xaa Pro Val Ile Thr
1               5

( 2 ) INFORMATION FOR SEQ ID NO:25:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note= "TABLE 2, PEPTIDE 3"

( x i ) SEQUENCE DESCRIPTION: SEQ ID NO:25:

Ile Ile Gly Gly Gly Ile Ala Thr Pro His Ser Xaa Pro Xaa Met Val
1               5                   10                  15

Gly Ile Phe ( 2 ) INFORMATION FOR SEQ ID NO:26:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..37
        ( D ) OTHER INFORMATION: /note= "TABLE 2, PEPTIDE 5"

( x i ) SEQUENCE DESCRIPTION: SEQ ID NO:26:

Val Xaa Val Val Thr Ala Ala His Cys Leu Val Thr Gln Phe Gly Asn
1               5                   10                  15

Arg Gln Xaa Tyr Ser Ile Phe Val Arg Val Gly Ala His Xaa Ile Xaa
                20                  25                  30

Asn Ser Gly Thr Asn
            35

( 2 ) INFORMATION FOR SEQ ID NO:27:

( i ) SEQUENCE CHARACTERISTICS:
   ( A ) LENGTH: 11 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..11
   ( D ) OTHER INFORMATION: /note= "TABLE 2, PEPTIDE 6"

( x i ) SEQUENCE DESCRIPTION: SEQ ID NO:27:

```
Val Val Ile Thr Gly Trp Gly Val Thr Gly Lys
1               5                   10
```

( 2 ) INFORMATION FOR SEQ ID NO:28:

( i ) SEQUENCE CHARACTERISTICS:
   ( A ) LENGTH: 18 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..18
   ( D ) OTHER INFORMATION: /note= "TABLE 2, PEPTIDE 7"

( x i ) SEQUENCE DESCRIPTION: SEQ ID NO:28:

```
Asn Val Leu Arg Glu Leu Glu Leu Pro Val Val Thr Asn Glu Gln Cys
1               5                   10                  15
Xaa Lys
```

( 2 ) INFORMATION FOR SEQ ID NO:29:

( i ) SEQUENCE CHARACTERISTICS:
   ( A ) LENGTH: 9 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..9
   ( D ) OTHER INFORMATION: /note= "TABLE 2, PEPTIDE 8"

( x i ) SEQUENCE DESCRIPTION: SEQ ID NO:29:

```
Ser Tyr Gln Thr Leu Pro Phe Ser Lys
1               5
```

( 2 ) INFORMATION FOR SEQ ID NO:30:

( i ) SEQUENCE CHARACTERISTICS:
   ( A ) LENGTH: 19 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..19
   ( D ) OTHER INFORMATION: /note= "TABLE 1, PEPTIDE 9"

( x i ) SEQUENCE DESCRIPTION: SEQ ID NO:30:

```
Leu Asn Arg Gly Ile Thr Asn Asp Met Ile Cys Ala Gly Phe Pro Glu
1               5                   10                  15

Gly Gly Lys
```

( 2 ) INFORMATION FOR SEQ ID NO:31:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..22
        ( D ) OTHER INFORMATION: /note= "TABLE 2, PEPTIDE 10"

( x i ) SEQUENCE DESCRIPTION: SEQ ID NO:31:

```
Asp Ala Cys Gln Gly Asp Ser Gly Gly Pro Leu Met Tyr Gln Asn Pro
1               5                   10                  15

Thr Thr Gly Arg Val Lys
                20
```

( 2 ) INFORMATION FOR SEQ ID NO:32:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..25
        ( D ) OTHER INFORMATION: /product="DNA SEQUENCE C"

( x i ) SEQUENCE DESCRIPTION: SEQ ID NO:32:

CGGAGCTCAA YGARCARTGY AAYAA        25

( 2 ) INFORMATION FOR SEQ ID NO:33:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..25
        ( D ) OTHER INFORMATION: /product="DNA SEQUENCE D"

( x i ) SEQUENCE DESCRIPTION: SEQ ID NO:33:

CGGAATTCGT NGGRTTYTGR TACAT        25

( 2 ) INFORMATION FOR SEQ ID NO:34:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide

```
        ( i x ) FEATURE:
                ( A ) NAME/KEY: Peptide
                ( B ) LOCATION: 1..4
                ( D ) OTHER INFORMATION: /note= "PEPTIDE MOTIF"

( x i ) SEQUENCE DESCRIPTION: SEQ ID NO:34:

Gln  Gln  Trp  Ser
        1
```

( 2 ) INFORMATION FOR SEQ ID NO:35:

```
        ( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..5
                ( D ) OTHER INFORMATION: /note= "A CHAIN PEPTIDE SEQUENCE
                        FROM FIG. 1"

( x i ) SEQUENCE DESCRIPTION: SEQ ID NO:35:

Val  Leu  Gly  Arg  Thr
        1                   5
```

( 2 ) INFORMATION FOR SEQ ID NO:36:

```
        ( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..5
                ( D ) OTHER INFORMATION: /note= "SECTION OF PEPTIDE C
                        SEQUENCE SET FORTH IN FIG.1"

( x i ) SEQUENCE DESCRIPTION: SEQ ID NO:36:

Val  Ser  Gly  Arg  Gly
        1                   5
```

( 2 ) INFORMATION FOR SEQ ID NO:37:

```
        ( i ) SEQUENCE CHARACTERISTICS:
                ( A ) LENGTH: 262 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Protein
                ( B ) LOCATION: 1..262
                ( D ) OTHER INFORMATION: /note= "BG1 A1 SEQUENCE (FIGURE 2)"

( x i ) SEQUENCE DESCRIPTION: SEQ ID NO:37:

Ala  Gly  Met  Asn  Leu  Ile  Trp  Gln  Asp  Glu  Phe  Asn  Gly  Thr  Thr  Leu
        1                   5                       10                      15

Asp  Thr  Ser  Lys  Trp  Asn  Tyr  Glu  Thr  Gly  Tyr  Tyr  Leu  Asn  Asn  Asp
                            20                      25                      30

Pro  Ala  Thr  Trp  Gly  Trp  Gly  Asn  Ala  Glu  Leu  Gln  His  Tyr  Thr  Asn
                            35                      40                      45
```

Ser  Thr  Gln  Asn  Val  Tyr  Val  Gln  Asp  Gly  Lys  Leu  Asn  Ile  Lys  Ala
     50                  55                      60

Met  Asn  Asp  Ser  Lys  Ser  Phe  Pro  Gln  Asp  Pro  Asn  Arg  Tyr  Ala  Gln
65                       70                      75                        80

Tyr  Ser  Ser  Gly  Lys  Ile  Asn  Thr  Lys  Asp  Lys  Leu  Ser  Leu  Lys  Tyr
               85                       90                          95

Gly  Arg  Val  Asp  Phe  Arg  Ala  Lys  Leu  Pro  Thr  Gly  Asp  Gly  Val  Trp
               100                      105                    110

Pro  Ala  Leu  Trp  Met  Leu  Pro  Lys  Asp  Ser  Val  Tyr  Gly  Thr  Trp  Ala
          115                      120                         125

Ala  Ser  Gly  Glu  Ile  Asp  Val  Met  Glu  Ala  Arg  Gly  Arg  Leu  Pro  Gly
     130                      135                    140

Ser  Val  Ser  Gly  Thr  Ile  His  Phe  Gly  Gly  Gln  Trp  Pro  Val  Asn  Gln
145                      150                         155                      160

Ser  Ser  Gly  Gly  Asp  Tyr  His  Phe  Pro  Glu  Gly  Gln  Thr  Phe  Ala  Asn
                    165                      170                         175

Asp  Tyr  His  Val  Tyr  Ser  Val  Val  Trp  Glu  Asp  Asn  Ile  Lys  Trp
               180                      185                    190

Tyr  Val  Asp  Gly  Lys  Phe  Phe  Tyr  Lys  Val  Thr  Asn  Gln  Gln  Trp  Tyr
          195                      200                    205

Ser  Thr  Ala  Ala  Pro  Asn  Asn  Pro  Asn  Ala  Pro  Phe  Asp  Glu  Pro  Phe
     210                 215                      220

Tyr  Leu  Ile  Met  Asn  Leu  Ala  Val  Gly  Gly  Asn  Phe  Asp  Gly  Gly  Arg
225                      230                    235                           240

Thr  Pro  Asn  Ala  Ser  Asp  Ile  Pro  Ala  Thr  Met  Gln  Val  Asp  Tyr  Val
               245                      250                         255

Arg  Val  Tyr  Lys  Glu  Gln
               260

( 2 ) INFORMATION FOR SEQ ID NO:38:

( i ) SEQUENCE CHARACTERISTICS:
        ( A ) LENGTH: 137 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..137
        ( D ) OTHER INFORMATION: /note= "XYN Z SEQUENCE (FIGURE 3)"

( x i ) SEQUENCE DESCRIPTION: SEQ ID NO:38:

Asn  Thr  Arg  Ile  Glu  Ala  Glu  Asp  Tyr  Asp  Gly  Ile  Asn  Ser  Ser  Ser
1              5                        10                           15

Ile  Glu  Ile  Ile  Gly  Val  Pro  Glu  Gly  Gly  Arg  Gly  Ile  Gly  Tyr
               20                  25                      30

Ile  Thr  Ser  Gly  Asp  Tyr  Leu  Val  Tyr  Lys  Ser  Ile  Asp  Phe  Gly  Asn
          35                      40                       45

Gly  Ala  Thr  Ser  Phe  Lys  Ala  Lys  Val  Ala  Asn  Ala  Asn  Thr  Ser  Asn
     50                      55                      60

Ile  Glu  Leu  Arg  Leu  Asn  Gly  Pro  Asn  Gly  Thr  Leu  Ile  Gly  Thr  Leu
65                       70                      75                          80

Ser  Val  Lys  Ser  Thr  Gly  Asp  Trp  Asn  Thr  Tyr  Glu  Glu  Gln  Thr  Cys
               85                      90                          95

Ser  Ile  Ser  Lys  Val  Thr  Gly  Ile  Asn  Asp  Leu  Tyr  Leu  Val  Phe  Lys

-continued

```
                      100                           105                             110
        Gly Pro Val Asn Ile Asp Trp Phe Thr Phe Gly Val Glu Ser Ser Ser
                115                     120                 125
        Thr Gly Leu Gly Asp Leu Asn Gly Asp
        130                     135
```

( 2 ) INFORMATION FOR SEQ ID NO:39:

( i ) SEQUENCE CHARACTERISTICS:
        ( A ) LENGTH: 127 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..127
        ( D ) OTHER INFORMATION: /note= "XLN A SEQUENCE (FIGURE 4)"

( x i ) SEQUENCE DESCRIPTION: SEQ ID NO:39:

```
        Ala Asp Gly Gly Gln Ile Lys Gly Val Gly Ser Gly Arg Cys Leu Asp
        1                   5                   10                  15

Val Pro Asp Ala Ser Thr Ser Asp Gly Thr Gln Leu Gln Leu Trp Asp
                        20                  25                  30

Cys His Ser Gly Thr Asn Gln Gln Trp Ala Ala Thr Asp Ala Gly Glu
                    35                  40                  45

Leu Arg Val Tyr Gly Asp Lys Cys Leu Asp Ala Ala Gly Thr Ser Asn
                50              55                  60

Gly Ser Lys Val Gln Ile Tyr Ser Cys Trp Gly Gly Asp Asn Gln Lys
        65                  70                  75                  80

Trp Arg Leu Asn Ser Asp Gly Ser Val Val Gly Val Gln Ser Gly Leu
                        85                      90                  95

Cys Leu Asp Ala Val Gly Asn Gly Thr Ala Asn Gly Thr Leu Ile Gln
                    100                 105                 110

Leu Tyr Thr Cys Ser Asn Gly Ser Asn Gln Arg Trp Thr Arg Thr
                    115                 120                 125
```

HORSESHOE CRAB AMEBOCYTE LYSATE FACTOR G SUBUNIT A

FIELD OF THE INVENTION

This invention relates to a polypeptide derived from limulus (horseshoe crab) amebocytes shown by an amino acid sequence of $(1\rightarrow3)$-$\beta$-D-glucan sensitive factor (hereinafter abbreviated as factor G) and a DNA encoding thereof, particularly to a polypeptide shown by an amino acid sequence of subunit a of factor G and a DNA encoding thereof.

BACKGROUND OF THE INVENTION

Heretofore, determination of endotoxin with a limulus amebocyte lysate has been known. This method is based on coagulation of lysate with a very small amount of endotoxin, for example at about $10^{-9}$ g. It has been elucidated with the progress of biochemistry that this coagulation reaction consists of the stepwise activation mechanism of some coagulation factors. (Takanori Nakamura et al., Jpn. J. Bacteriol., 38, 781–803 (1983)). FIG. 1 shows the coagulation cascade reaction of Japanese horseshoe crab (*Tachypleus tridentatus*). The structures of three serine protease precursors (factor C, factor B and proclotting enzyme) and a clottable protein (coagulogen) in FIG. 1 have been elucidated by studies such as cDNA cloning (T. Muta et al. (1991) J. Biol. Chem., 265, 22426–22433 and 266, 6554–6561, and T. Miyata et al (1986) J. Biochem., 100, 213–220).

The lysate has been known to react with $(1\rightarrow3)$-$\beta$-D-glucan which exists in the cell walls of fungi and yeasts, at concentrations of $10^{-8}$–$10^{-9}$ g to trigger coagulation (see FIG. 1). Factor G responds to $(1\rightarrow3)$-$\beta$-D-glucans, initiating clot formation. It is reported that factor G is a serine protease precursor as well as the other factors and it is a glycoprotein composed of non-covalently associated subunits a (72 kDa) and b (37 kDa) (64th Annual Meeting of Japan Biochemical Society, 1991).

Additionally, subunit a of factor G has a specific binding site to $(1\rightarrow3)$-$\beta$-D-glucan and subunit b has serine protease region. Factor G is supposed to be activated and express serine protease activity by the binding of $(1\rightarrow3)$-$\beta$-D-glucan to subunit a. However, the complete structure of factor G remains unknown.

DISCLOSURE OF THE PRESENT INVENTION

The present invention was accomplished with these understandings and aims to isolate and purify the factor G derived from limulus amebocytes, particularly subunit a having a binding site with $(1\rightarrow3)$-$\beta$-D-glucan and to elucidate its complete structure.

Another object of the present invention is to provide a polypeptide having a $(1\rightarrow3)$-$\beta$-D-glucan binding site of a factor G and a DNA encoding thereof.

The other object of the present invention is to provide a polypeptide of subunit a of factor G and DNA encoding thereof.

Further object of the present invention is to provide a polypeptide of factor G containing subunit a and a DNA encoding thereof.

Therefore, the present invention relates to a single stranded DNA encoding for a polypeptide containing at least one motif structure shown by an amino acid sequence of (SEQ. ID No:34): Gln-Gln-Trp-Ser, a double stranded DNA composed of said DNA and its complementary DNA, and a polypeptide shown by said amino acid sequence.

Furthermore, the present invention relates to a single stranded DNA encoding for a polypeptide consisted of below mentioned amino acid sequence or a homologous sequence thereof, a double stranded DNA composed of said DNA and its complementary DNA and a polypeptide shown by said amino acid sequence (SEQ. ID No.2):

| | | | | | | | | | | | | | | |
|---|---|---|---|---|---|---|---|---|---|---|---|---|---|---|
| Ser | His | Glu | Pro | Lys | Trp | Gln | Leu | Val | Trp | Ser | Asp | Glu | Phe | Thr |
| Asn | Gly | Ile | Ser | Ser | Asp | Trp | Glu | Phe | Glu | Met | Gly | Asn | Gly | Leu |
| Asn | Gly | Trp | Gly | Asn | Asn | Glu | Leu | Gln | Tyr | Tyr | Arg | Arg | Glu | Asn |
| Ala | Gln | Val | Glu | Gly | Gly | Lys | Leu | Val | Ile | Thr | Ala | Lys | Arg | Glu |
| Asp | Tyr | Asp | Gly | Phe | Lys | Tyr | Thr | Ser | Ala | Arg | Leu | Lys | Thr | Gln |
| Phe | Asp | Lys | Ser | Trp | Lys | Tyr | Gly | Lys | Ile | Glu | Ala | Lys | Met | Ala |
| Ile | Pro | Ser | Phe | Arg | Gly | Val | Trp | Val | Met | Phe | Trp | Met | Ser | Gly |
| Asp | Asn | Thr | Asn | Tyr | Val | Arg | Trp | Pro | Ser | Ser | Gly | Glu | Ile | Asp |
| Phe | Ile | Glu | His | Arg | Asn | Thr | Asn | Asn | Glu | Lys | Val | Arg | Gly | Thr |
| Ile | Ile | Trp | Ser | Thr | Pro | Asp | Gly | Ala | His | Ala | His | His | Asn | Arg |
| Glu | Ser | Asn | Thr | Asn | Gly | Ile | Asp | Tyr | His | Ile | Tyr | Ser | Val | Glu |
| Trp | Asn | Ser | Ser | Ile | Val | Lys | Trp | Phe | Val | Asn | Gly | Asn | Gln | Tyr |
| Phe | Glu | Val | Lys | Ile | Gln | Gly | Gly | Val | Asn | Gly | Lys | Ser | Ala | Phe |
| Arg | Asn | Lys | Val | Phe | Val | Ile | Leu | Asn | Met | Ala | Ile | Gly | Gly | Asn |
| Trp | Pro | Gly | Phe | Asp | Val | Ala | Asp | Glu | Ala | Phe | Pro | Ala | Lys | Met |
| Tyr | Ile | Asp | Tyr | Val | Arg | Val | Tyr | Gln | Asp | Ala | Ser | Thr | Ser | Ser |
| Pro | Val | Gly | Asp | Thr | Ser | Leu | Asp | Gly | Tyr | Tyr | Phe | Val | Gln | Asn |
| Arg | His | Ser | Glu | Leu | Tyr | Leu | Asp | Val | Thr | Asp | Ala | Ser | Asn | Glu |
| Asp | Gly | Ala | Phe | Leu | Gln | Gln | Trp | Ser | Tyr | Ser | Gly | Asn | Glu | Asn |
| Gln | Gln | Phe | Asp | Phe | Glu | His | Leu | Gln | Asn | Asn | Val | Tyr | Lys | Ile |
| Thr | Asn | Lys | Lys | Ser | Gly | Lys | Ser | Leu | Asp | Val | Tyr | Asn | Phe | Gly |
| Thr | Glu | Asn | Gly | Val | Arg | Ile | Gln | Gln | Trp | Ser | Tyr | Gly | Gly | Ala |
| Arg | Asn | Gln | Gln | Phe | Thr | Val | Gln | Ser | Val | Gly | Asp | Gly | Tyr | Tyr |
| Lys | Ile | Ile | Pro | Arg | Gly | Ser | Gly | Lys | Leu | Val | Glu | Val | Ala | Asp |
| Phe | Ser | Lys | Asp | Ala | Gly | Gly | Lys | Ile | Gln | Gln | Trp | Ser | Asp | Asn |
| Asn | Gln | Leu | Ser | Gly | Gln | Trp | Lys | Leu | Ile | Lys | Ser | Lys | Ser | Tyr |
| Ser | Lys | Leu | Ile | Gln | Ala | Glu | Ser | Tyr | Phe | Asp | Ser | Ser | Lys | Val |
| Gln | Leu | Glu | Asp | Thr | Ser | Asp | Val | Gly | Gly | Gly | Lys | Asn | Val | Lys |
| Cys | Asp | Asn | Glu | Gly | Ala | Trp | Met | Ala | Tyr | Lys | Asp | Ile | Asp | Phe |
| Pro | Ser | Ser | Gly | Asn | Tyr | Arg | Ile | Glu | Tyr | Arg | Val | Ala | Ser | Glu |
| Arg | Ala | Gly | Gly | Lys | Leu | Leu | Ser | Leu | Asn | Ala | Asn | Ala | Ser | Ile |
| Val | Leu | Gly | Met | Leu | Asp | Val | Pro | Ser | Thr | Gly | Gly | Trp | Gln | Lys |
| Trp | Thr | Thr | Ile | Ser | His | Thr | Val | Asn | Val | Asp | Ser | Gly | Thr | Tyr |

-continued

| | | | | | | | | | | | | | | |
|---|---|---|---|---|---|---|---|---|---|---|---|---|---|---|
| Asn | Leu | Gly | Ile | Tyr | Val | Gln | Arg | Ala | Ser | Trp | Asn | Ile | Asn | Trp |
| Ile | Lys | Ile | Thr | Lys | Ile | Pro | Glu | Gln | Ser | Asn | Leu | Asn | Gln | Gly |
| Arg | Arg | Asn | Ser | Lys | Leu | Ile | Gln | Ala | Glu | Ser | Tyr | Phe | Ser | Tyr |
| Ser | Glu | Val | Gln | Leu | Glu | Asp | Thr | Leu | Asp | Val | Gly | Gly | Gly | Lys |
| Asn | Val | Lys | Cys | Asp | Lys | Glu | Gly | Ala | Trp | Met | Ala | Tyr | Lys | Asp |
| Ile | Asp | Phe | Pro | Ser | Ser | Gly | Ser | Tyr | Arg | Val | Glu | Tyr | Arg | Val |
| Ala | Ser | Glu | Arg | Ala | Gly | Gly | Lys | Leu | Ser | Leu | Asp | Leu | Asn | Ala |
| Gly | Ser | Ile | Val | Leu | Gly | Met | Leu | Asp | Ile | Pro | Ser | Thr | Gly | Gly |
| Leu | Gln | Lys | Trp | Thr | Thr | Ile | Ser | His | Ile | Val | Asn | Val | Asp | Leu |
| Gly | Thr | Tyr | Asn | Leu | Gly | Ile | Tyr | Val | Gln | Lys | Ala | Ser | Trp | Asn |
| Ile | Asn | Trp | Ile | Arg | Ile | Thr | Lys | Val | | | | | | |

Four species of horseshoe crab have been known and the coagulogens which are components of amebocytes of these four species of horseshoe crab are very similar in their structure (73%–9%) that is necessary for the expression of their function. Thus, the polypeptides of the present invention derived from these four species of horseshoe crab are presumed to have similar amino acid sequence as well as that in coagulogen.

In other words, where there is a homology between polypeptides, there is an identical or similar functional expression with their similar amino acid sequences though they have no identical amino acid sequences. Therefore, person skilled in the art will easily understand that the present invention encompasses not only the above mentioned amino acid sequence but also its homologous amino acid sequences.

The present invention will be explained in detail.

Factor G can be isolated and purified from amebocyte lysate of horseshoe crab by various column chromatography techniques, for example, affinity chromatography with dextran sulfate-Sepharose$^{RTM}$ CL-6B and Concanavalin A-Sepharose$^{RTM}$ 4B, gel filtration chromatography such as Sephacryl$^{RTM}$ S-200HR (T. Morita et al. (1981) FEBS Lett., 129(2), 318–321, Japanese Published Examined Patent Application (herein after abbreviated as Japan Tokkyo Koho) No. 399 (1991). Furthermore, subunits a and b which constitute factor G can be obtained by denaturation of factor G with a denaturing agent such as a surfactant followed by fractionation with high performance liquid chromatography (hereinafter abbreviated as HPLC) using a molecular sieve. The partial amino acid sequences of the each subunits can be determined by the following; each subunit is subjected to reduction and alkylation and enzymic digestion to give peptide fragments, and the amino acid sequence of the peptide fragments is determined by a peptide sequencer and so on. cDNAs encoding for the each subunits are isolated from the cDNA libraries, which are prepared from poly(A)$^+$ RNA isolated from limulus amebocytes, using antibodies to each subunits or oligonucleotides synthesized according to aforementioned partial amino acid sequences of each subunits. Then the nucleotide sequence of these cDNA can be determined using dideoxy chain termination method (Sanger, F. et al., Proc. Natl. Acad. Sci. U.S.A., 74, 5463–5467 (1977)). The amino acid sequences of each subunits can be determined from above mentioned nucleotide sequences and partial amino acid sequences.

cDNA (AGC . . . GTG; base Nos. 114–2,075) encoding for polypeptide of subunit a of factor G shown in sequence No. 1 and the corresponding amino acid sequence (Ser . . . Val; amino acid Nos. 1–654) are determined according to the above mentioned method.

Further, subunit a of factor G was found to have a domain structure from its amino acid sequence.

That is, a glucanase domain having amino acid sequence similar to that of carboxyl terminal of β-1,3-glucanase was found in the amino terminal of subunit a (Pro . . . Ala; amino acid Nos. 4–236) (FIG. 2). While, the carboxyl terminal portion of subunit a has a repetitive structure composed of 126 amino acids (Ser . . . Ile; amino acid Nos. 391–516 and Ser . . . Val; amino acid Nos. 529–654), and this sequence is similar to that of amino terminal portion of xylanase Z (FIG. 3). Furthermore, a "QQWS (Gln-Gln-Trp-Ser)" SEQ. ID No.34motif is contained between domains of glucanase and xylanase, and three repetitions of a sequence similar to that of xylanase A (Leu . . . Leu; amino acid Nos. 247–293, Glu . . . Val; amino acid Nos. 294–340 and Gly . . . Ser; amino acid Nos. 341–387) (FIG. 4).

Additionally, FIG. 2–4 showed each amino acid with one letter code.

In the present invention, recombinant DNA vectors including the DNA encoding for these peptides are prepared and transfected into hosts and cultured or bred with so-called gene technology to produce and collect desired peptides.

BRIEF EXPLANATION OF THE DRAWINGS

FIG. 2 shows the amino acid sequence of glucanase domain of subunit a (amino acid Nos. 4–236). In the Fig., FGA indicates an amino acid sequence of amino acid Nos. 4–236 of subunit a of factor G, and : Gl Al indicates an amino acid sequence of amino acid Nos. 421–682 of β-1, 3-glucanase.

FIG. 3 shows a domain of amino acid Nos. 391–654 in subunit a of factor G. In the Fig., FGA indicates an amino acid sequence of amino acid Nos. 391–654 of subunit a of factor G, and Xyn Z indicates an amino acid sequence of amino acid Nos. 298–434 of xylanase Z.

FIG. 4 shows a domain of amino acid Nos. 247–387 of subunit a of factor G. In the Fig., FGA indicates an amino acid sequence of amino acid Nos. 247–387 of subunit a of factor G, and Xln A indicates an amino acid sequence of amino acid Nos. 351–477 of xylanase A.

THE BEST MODE TO PERFORM THE INVENTION

Figure 1:
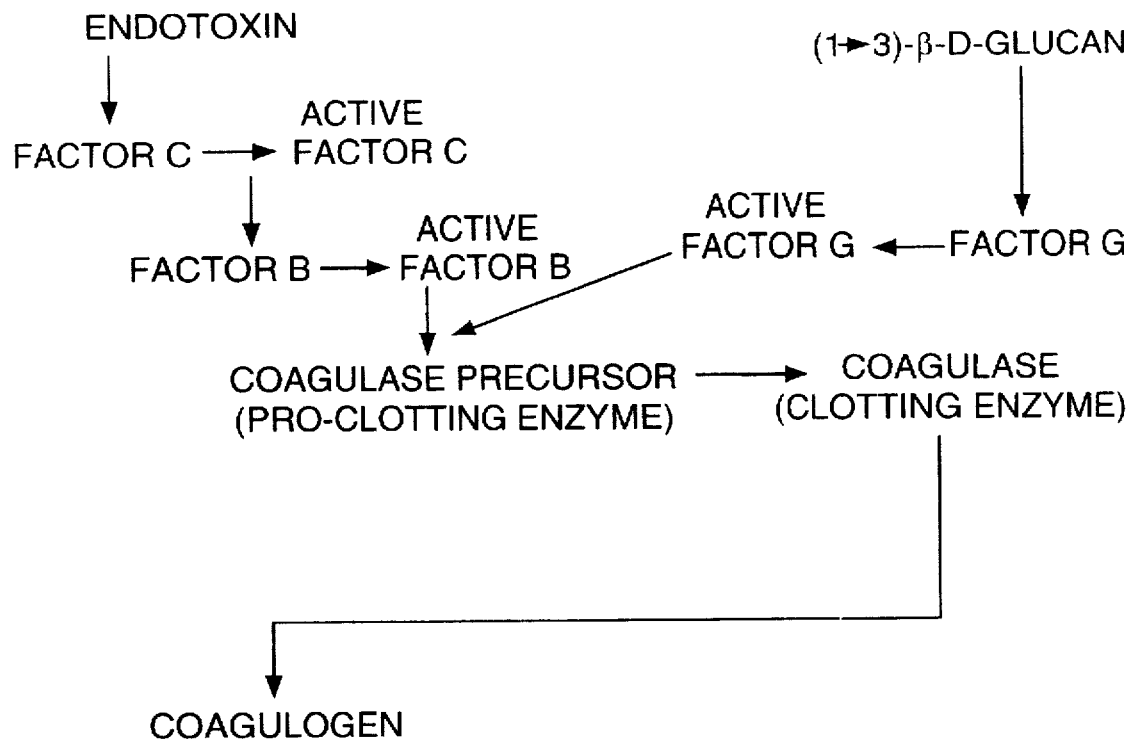
FIG. 1 shows the mechanisms of endotoxin sensitive and (1→3)-β-D-glucan sensitive coagulation cascade reaction of horseshoe crab amebocyte.
Figure 1:
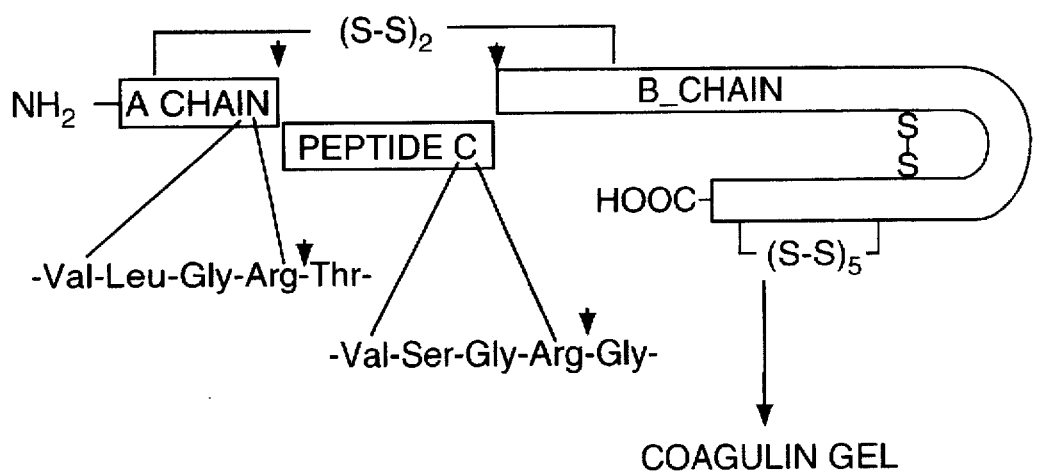

The present invention will be explained by the following practical examples, however, the scope of the invention is not restricted by these examples.

EXAMPLE 1

1. Purification of Factor G (1) Preparation of amebocyte lysate 400 ml of 0.02M Tris-HCl buffer containing 50 mM NaCl, pH 8.0 was added to 113 g of amebocytes of Tachypleus tridentatus, and homogenized for three minutes with a high speed homogenizer (Hyscotron$^{RTM}$, Nippon Seimitsu Kogyo Co., Ltd.) and then centrifuged at 8,000 rpm for 30 min. to obtain a supernatant. Further, 300 ml of the same buffer was added to the resultant precipitates, homogenized and centrifuged in a similar manners to obtain a supernatant. The similar procedure was repeated further twice. All supernatants obtained by centrifugation were combined and 1,250 ml of amebocyte lysate was obtained.

(2) Purification of factor G from the amebocyte lysate.

a. Dextran sulfate-Sepharose$^{RTM}$ CL-6B column chromatography.

The obtained 1,250 ml of extract was applied to a dextran sulfate-Sepharose$^{RTM}$ CL-6B column (5×17.8 cm) equilibrated in advance with the extraction buffer. The preparation of the column is performed according to the method shown in Japan Tokkyo koho No. 399 (1991) preparative example 2. The applied column was washed thoroughly with the same buffer and washed with 0.02M Tris-HCl buffer containing 0.15M NaCl, pH 8.0, to wash out the excess amount of protein which adsorbed into the column. The adsorbed protein into the column was eluted with 0.02M Tris-HCl buffer containing 0.25M NaCi, pH 8.0, to obtain factor G fraction.

b. Concanavalin A-Sepharose$^{RTM}$ 4B column chromatography.

The above mentioned factor G fraction was applied to a Con A-Sepharose$^{RTM}$ 4B column (Pharmacia Biotech K.K.) (2×16 cm) equilibrated with 0.02M Tris-HCl buffer containing 0.25M NaCi, pH 8.0, washed thoroughly with the equilibration buffer and 0.02M Tris-HCl buffer containing 0.5M NaCl, pH 8.0, successively, then, the protein which adsorbed into the column was eluted with 0.02M Tris-HCl buffer containing 0.5M each of NaCl and methyl α-D-glucoside, pH 8.0, to obtain factor G fraction.

c. Sephacryl$^{RTM}$ S-200 HR column chromatography

The above mentioned factor G fraction was concentrated with ultrafiltration and applied to a Sephacryl$^{RTM}$ S-200 HR column (Pharmacia Biotech K.K.) (2.7×98 cm) equilibrated with 0.05M sodium phosphate buffer, pH 6.5, and protein was eluted with the same buffer. The final eluate fraction of this chromatography containing the protein with slight absorbance at 280 nm was collected to obtain the protein of finally purified preparation of factor G. About 300 μg of factor G calculated as bovine serum albumin was obtained from 113 g of amebocytes.

2. Determination of Partial Ssequence of Subunit a of Factor G (1) Separation of subunits a and b of factor G Subunits a and b of factor G were separated for the elucidation of partial amino acid sequences of subunits a and b required for cDNA cloning of subunits a and b of factor G. The factor G obtained in the above mentioned 1 was precipitated with methanol and chloroform for desalting and concentration (Methods in Enzymology, 182, p. 78–79 (1990)). The resultant precipitates were dissolved in 2% sodium dodecylsulfate (SDS) solution, and heated at 100° C. for 5 min. This heated sample was applied to gel filtration by using a tandem columns of TSKgeI$^{RTM}$ G3000SW (TOSOH Corp.) using 0.1M sodium phosphate buffer containing 0.1% SDS, pH 7.0, as a mobile phase, and subunits a and b of factor G were separated.

(2) Enzymic digestion of subunit a of factor G

Trichloroacetic acid (TCA) was added to give final concentration of 17.4 w/v % into the fraction of subunit a of factor G which obtained by above mentioned 2(1), and subunit a of factor G was precipitated. According to the method of Paul Matsudaira (A Practical Guide to Protein and Peptide Purification for Microsequencing, p. 42–43, 1989, Academic Press, Inc.), the precipitated subunit a of factor G was dissolved in 0.4M ammonium bicarbonate containing 8M urea and caused to reduction and alkylation with iodoacetamide. The reaction mixture was added with water to give 4M urea concentration, and lysyl endopeptidase (Wako Pure Chemical Ind. Ltd.) was added at an enzyme-suibstrate weight ratio of 1:60 and digestion was performed at 37° C. for 20 hrs. The digested product was applied to a μBondasphere$^{RTM}$ 5μC8-300 angstrom (Waters Co., Ltd.) column (2.1×150 mm) preliminarily equilibrated with 0.06 v/v % trifluoroacetic acid and the column was thoroughly washed and eluted with acetonitrile using a linear concentration gradient method of 0 v/v % at 5 min., 24 v/v % at 65 min., 56 v/v % at 125 min. and 80 v/v % at 135 min. at a flow rate of 0.2 ml/min. to elute the adsorbed protein. The eluted peptides were monitored with UV absorbance at 210 nm, and completely collected.

(3) Determination of partial amino acid sequence.

The amino acid sequence of obtained each peptide was determined with a gas phase sequencer Model 477A (Applied Biosystems Japan Inc.). The results are shown in Table 1.

TABLE 1

Peptide 1 (SEQ. ID NO.5)
    Ser—Xaa—Glu—Pro—Lys—Xaa—Gln—Leu—Val—

Peptide 2 (SEQ. ID NO.6)
    Arg—Glu—Asp—Tyr—Asp—Gly—Phe—Lys

Peptide 3 (SEQ. ID NO.7)
    Tyr—Thr—Ser—Ala—Arg—Leu—Lys

Peptide 4 (SEQ. ID NO.8)
    Thr—Gln—Phe—Asp—Lys

Peptide 5
    Ser—Trp—Lys

Peptide 6
    Tyr—Gly—Lys

Peptide 7 (SEQ. ID NO.9)

TABLE 1-continued

Met — Ala — Ile — Pro — Ser — Phe — Arg — Gly — Val — Trp — Val — Met — Phe —
Trp — Met — Ser — Gly — Xaa — Asn — Thr — Asn — Tyr — Val — Xaa — Xaa — Pro —

Peptide 8 (SEQ. ID NO.10)
    Ser — Ala — Phe — Arg — Asn — Lys

Peptide 9 (SEQ. ID NO.11)
    Val — Phe — Val — Ile — Leu — Asn — Met — Ala — Ile — Gly — Gly — Asn — Xaa —
    Pro — Gly — Phe — Xaa — Val — Ala —

Peptide 10 (SEQ. ID NO.12)
    Ile — Ile — Pro — Arg — Gly — Ser — Gly — Lys

Peptide 11 (SEQ. ID NO.13)
    Val — Gln — Leu — Glu — Asp — Thr — Ser — Asp — Val — Gly — Gly — Gly — Lys Peptide 12 (SEQ. ID NO.14)
    Cys — Asp — Asn — Glu — Gly — Ala — Trp — Met — Ala — Tyr — Lys Peptide 13 (SEQ. ID NO.15)
    Asp — Ile — Asp — Phe — Pro — Ser — Ser — Gly — Asn — Tyr — Xaa — Ile — Glu —
    Tyr — Xaa — Val — Ala —

Peptide 14 (SEQ. ID NO.16)
    Leu — Ile — Gln — Ala — Glu — Xaa — Tyr — Phe — Xaa — Tyr — Xaa — Glu — Val —
    Gln — Leu — Glu —

Peptide 15 (SEQ. ID NO.17)
    Glu — Gly — Ala — Trp — Met — Ala — Tyr — Lys

Peptide 16 (SEQ. ID NO.18)
    Val — Arg — Gly — Thr — Ile — His — Trp — Ser — Thr — Pro — Asp — Gly — Ala —
    His — Ala — His — His — Asn — Arg —

In the formula, Xaa represents one of naturally occurring amino acids.

3. Synthesis of Oligonucleotide

In the determined amino acid sequences shown in Table 1, two amino acid sequences A (SEQ. ID No.6): -Glu-Asp-Tyr-Asp-Gly-Phe- and B(SEQ. ID No.9): -Trp-Val-Met-Phe-Trp-Met- were selected and reverse translated as a sense in the case of A and as an antisense in the case of B. A mixture of 25 mer and 26 mer oligonucleotides shown below having recognition sequence of restriction enzyme and two bases for protection of DNA at 5'-terminal were synthesized with a DNA synthesizer 380A (Applied Biosystems Japan Inc.).

```
                                                      [Formula 1]
A': 5'-CGGAGCTCGAAGATTATGATGGTTT-3' 25 mer
              G  C  C  C  C         (SEQ. ID NO.19)
                       A
                       G B': 3'-ACCCATTACAAAACCTACCTTAAGGC-5' 26 mer
              C        G             (SEQ. ID NO.20)
              A
              G
```

The oligonucleotides A' and B' shown above include all possibilities of sequences corresponding to A and B or complementary sequences thereof (however, the third nucleotide (T, C) in codon of Phe in A (TT(C/T)) was excluded).

4. Preparation of PolY(A)$^+$ RNA Containing mRNA Encoding for Factor G

Since poly(A)$^+$ RNA was isolated from amebocytes of horseshoe crab, factor G is purified from amebocytes of horseshoe crab.

(1) Preparation of total RNA

By using of AGPC method (Experimental Medicine (Jikken Igaku) 9, 1937–1940 (1991), Pub. by Yodosha Co., Ltd.), about 11 mg of total RNA was isolated from 11.8 g of limulus amebocytes.

(2) Preparation of poly(A)$^+$ RNA Poly(A)$^+$ RNA was isolated from about 2 mg of the above mentioned total RNA with Oligotex-dT$^{RTM}$ 30 Super kit (Nippon Roche K.K.). The similar procedure was repeated once again for further purification to obtain 34.5 µg of highly purified poly(A)$^+$ RNA from 2 mg of total RNA.

5. Preparation of cDNA Library of Amebocytes of Horseshoe crab (1) Synthesis of cDNA cDNA was synthesized from 5 µg in 34.5 µg of poly(A)$^+$ RNA obtained in the above mentioned 4 with a cDNA synthesis kit (Amersham Co. Ltd.).

(2) Preparation of cDNA library cDNA library of amebocytes of horseshoe crab was prepared from cDNA synthesized in the above mentioned (1) by a cDNA cloning system λgt10 adapter method (Amersham Co. Ltd.).

6. cDNA cloning of subunit a of factor G cDNA fragment encoding for a part of subunit a of factor G was amplified with the oligonucleotide prepared in the above mentioned 3 using poly(A)$^+$ RNA prepared in the above mentioned 4 (2) as a template by PCR method (Saiki, R. K., et al. Science, 239, 487–491, (1988)). The amplified cDNA fragment was labeled with [α-$^{32}$P]dCTP using Multiprime-DNA labeling kit (Nippon Gene Co., Ltd.) to obtain a probe. The probe was used for the screening of cDNA library prepared in above mentioned 5 (2) to obtain two positive clones containing a longest insert cDNA having about 2,400 bp. The insert cDNA of these clones were almost identical except for the length difference of 5'- and 3'-terminals in several bases, and their nucleotide sequences were determined. The composite nucleotide sequence contained an initiation codon and poly(A)$^+$ tail, and showed the length of 2,408 bp.

7. Determination of Nucleotide Sequence of cDNA Encoding for Subunit a of Factor G The insert cDNA prepared in the above mentioned 6 was integrated in pUC118 vector and pBluescript Π SK vector. The determination of total nucleotide sequences of cDNA cloned in pUC118 vector and pBluescript Π SK vector was performed by subcloning with deletion using restriction enzyme recognition site on cDNA fragment and kilo-sequence deletion kit (Takara Shuzo Co., Ltd.). The nucleotide sequence of cDNA in the clone prepared by the above mentioned procedure was determined with a DNA sequencer 370A (Applied Biosystems Japan Inc.) using fluorolabeled nucleotide primer (Smith, L. M. et al. (1986), Nature 321, 674–679).

The determined nucleotide sequence of cDNA of subunit a of factor G, and the deduced amino acid sequence were shown in SQ ID No. 1 of the Sequence listing. The partial amino acid sequences determined in 2 (3) (Table 1) are all included in the above mentioned amino acid sequence, and the inserted cDNA whose nucleotide sequence was determined by the procedure, was confirmed its encoding of subunit a of factor G.

8. Expression and Purification of Factor G or Subunits Thereof

Whole or partial gene encoding for subunit a of factor G was cut out from the clone obtained above with ultrasonic wave or restriction enzyme treatment, or the other methods known in the art and integrated to a suitable vector. Vectors which constructed from such as phages or plasmids which autonomously proliferate in host microorganisms or cells for gene recombination including suitable promoters, SD sequences, translation initiating codon ATG, and suitable structural gene can be preferably used. These constructed vectors are integrated to obtain transformants in a suitable host organisms or cells, such as various strains of *E. coli* and yeasts, animal cells (e.g. oocytes of mice and rats, Chinese hamster oocytes (CHO)), plant cells and insect cells or animal, plant or insect hosts. The resultant transformant is cultured in a nutrient medium or bred with nutrient feeds to have stable production of large amount of factor G or subunit thereof (hereinafter abbreviated as factor G etc.). Culture or breeding conditions of the transformant may be suitably modified within the scope of factor G etc. production and conventional conditions known well to persons skilled in the art for the growth of hosts can be preferably used. Factor G etc. in the cultured products or bred animals can be collected from extracts of mechanically ground cultured solution containing microorganisms or cells, or individuals. However, when factor G etc. exist in the cultured solutions or extracts, factor G etc. are generally used after separating solutions containing factor G etc. from microorganisms, cells or ground individuals by filtration or centrifugation. When factor G etc. exist in microorganisms, cells, or organ membranes of individuals, microorganisms, cells or particles are collected by the filtration or centrifugation of the obtained cultured products or particles, and solubilized by mechanical or ultrasonic treatment, enzymic treatment with lysozyme and so on, addition of a chelating agent such as EDTA and/or a surfactant to separate and collect the factor G etc. The solutions containing factor G etc. obtained above can be isolated by conventional protein purification methods.

Factor G etc. expressed as a chimera polypeptide can be easily isolated by application of the properties of the other proteins. For example, the aimed factor G etc. can be easily isolated with affinity chromatography by applying the affinity of the other proteins.

Practically, subunit a of factor G can be expressed by the following procedure.

An oligonucleotide having a sequence of (SEQ. ID No.21)5'-AGCCACGAACCAAAGTGGCA-3' is synthesized and its 5'-terminal is phosphorylated. The resultant oligonucleotide is annealed with a single-stranded DNA prepared from a plasmid integrated with a gene encoding for the subunit a of factor G, and elongation reaction was performed with DNA polymerase such as Klenow fragment. The single-stranded portion produced in this procedure is digested with a DNA nuclease such as Mung bean nuclease to obtain a double-stranded DNA. The resultant double-stranded DNA is digested with Sph I restriction enzyme and the produced cohesive ends are blunted with T4 DNA polymerase, Klenow fragment or Blunting kit. This double-stranded DNA is preliminarily digested with Nco I restriction enzyme and then the resultant cohesive end is integrated to pTV118N contained ampicillin resistant gene which was blunted with T4 DNA polymerase, Klenow fragment or a Blunting kit. The produced plasmid is transfected into *E. coli* JM109 or *E. coli* MV1184 to obtain transformant. The aimed transformant can be selected by applying conventional methods using the properties of plasmid. That is, a transformed microorganism is cultured on a LB plate contained ampicillin which is preliminarily sprayed with 5-bromo-4-chloro-3-(3-indolyl)-β-D-galactoside (X-gal)/isopropylthiogalactoside (IPTG) and white colonies which transducted with the aimed plasmid are picked up and selected. Further screening with a synthetic oligonucleotide probe of (SEQ. ID No.22)5'-AAACAGACCATGAGCCACGAACCA-3' gave the plasmid with correct sequence. Furthermore, it can be confirmed by DNA sequencing with a sequencing primer using RV-N primer (Takara Shuzo Co., Ltd.) whether the plasmid was constructed correctly. *E. coli* JM109 or *E. coli* MV1184 transfected with the plasmid with correct sequence is cultured in a 3% Nutrient broth (Nissui Pharmaceutical Co., Ltd.) containing 100 µg/ml ampicillin and 1 mM IPTG at 30° C. for 24 hrs. Subunit a of factor G is purified the cultured supernatant or extract of microorganisms by conventional methods. An affinity chromatography with antibody or a ligand having affinity to subunit a of factor G is preferably used for the more simple purification.

EXAMPLE 2

1. Determination of Partial Amino Acid Sequence of Subunit b of Factor G (1) Isolation of subunit b of factor G Subunit b can be similarly isolated according to Example 1, 2. (1) by separation of subunits a and b.

(2) Enzymic digestion of subunit b of factor G

Peptide fragments were obtained by the same method as Example 1, 2. (2) from subunit b of factor G obtained by above mentioned (1).

(3) Determination of partial amino acid sequence

The respective amino acid sequence of obtained peptides were determined by a similar manner to that of Example 1, 2. (3). The results are shown in Table 2.

TABLE 2

Peptide 1 (SEQ. ID NO.23)
  Gly — Ile — Asn — Glu — Lys

Peptide 2 (SEQ. ID NO.24)
  Xaa — Xaa — Gly — Phe — Xaa — Pro — Val — Ile — Thr —

Peptide 3 (SEQ. ID NO.25)
  Ile — Ile — Gly — Gly — Gly — Ile — Ala — Thr — Pro — His — Ser — Xaa — Pro — Xaa — Met — Val — Gly — Ile — Phe —

Peptide 4
Val — Asn — Pro —

Peptide 5 (SEQ. ID NO.26)
  Val — Xaa — Val — Val — Thr — Ala — Ala — His — Cys — Leu — Val — Thr — Gln — Phe — Gly — Asn — Arg — Gln — Xaa — Tyr — Ser — Ile — Phe — Val — Arg — Val — Gly — Ala — His — Xaa — Ile — Xaa — Asn — Ser — Gly — Thr — Asn —

Peptide 6 (SEQ. ID NO.27)
  Val — Val — Ile — Thr — Gly — Trp — Gly — Val — Thr — Gly — Lys Peptide 7 (SEQ. ID NO.28)
  Asn — Val — Leu — Arg — Glu — Leu — Glu — Leu — Pro — Val — Val — Thr — Asn — Glu — Gln — Cys — Xaa — Lys Peptide 8 (SEQ. ID NO.29)
  Ser — Tyr — Gln — Thr — Leu — Pro — Phe — Ser — Lys Peptide 9 (SEQ. ID NO.30)
  Leu — Asn — Arg — Gly — Ile — Thr — Asn — Asp — Met — Ile — Cys — Ala — Gly — Phe — Pro — Glu — Gly — Gly — Lys Peptide 10 (SEQ. ID NO.31)
  Asp — Ala — Cys — Gln — Gly — Asp — Ser — Gly — Gly — Pro — Leu — Met — Tyr — Gln — Asn — Pro — Thr — Thr — Gly — Arg — Val — Lys

2. Synthesis of Oligonucleotide

In the determined amino acid sequences, two amino acid sequences C: -Asn-Glu-Gln-Cys-(Asn)-Lys and D: -Met-Tyr-Gln-Asn-Pro-Thr- were used for reverse translation of C and D as sense and antisense, respectively, and the mixture of oligonucleotides C' and D' each having 25 nucleotides as shown below were synthesized in a similar manner to that of Example 1, 3. In the C, -(Asn)- means presumed as Asn.

[Formula 2]
C': 5'-CGGAGCTCAATGAACAATGTAATAA-3' 25 mer
         C   G   G   C      C           (SEQ. ID NO.32)

D': 3'-TACATAGTTTTAGGTTGCTTAAGGC-5' 26 mer
       G   C   G   C                    (SEQ. ID NO.33)
           A
           G The oligonucleotides C' and D' shown above include possibility of all the sequences corresponding to C and D, or complementary sequences. However, the C-terminal amino acid Lys of C and D, and Thr in D exclude the third nucleotides (A and G, and T, C, A, and G, respectively) in the respective codon of AA(A/G) and AC(A/C/G/T).

4. cDNA Cloning of Subunit b of Factor G

Using the poly(A)+ RNA obtained by Example 1, 4. (2) as a template and the oligonucleotide synthesized by the above mentioned 2, the experiment was performed in a similar manner to that of Example 1, 6., and a positive clone having 1,979 bp of cDNA was obtained. The nucleotide sequence of insertion cDNA in the clone was analyzed and included a nucleotide sequence corresponding to amino acid sequence of peptide derived from subunit b of factor G obtained by the above mentioned 1. (2), and poly A additional signal. The clone was presumed to have full length of cDNA from its size.

5. Determination of cDNA Nucleotide Sequence Encoding for Subunit b of Factor G The nucleotide sequence of cDNA of subunit b of factor G was determined by a similar manner to that of Example 1, 7. The determined nucleotide sequence of cDNA of subunit b of factor G and amino acid sequence determined from the nucleotide sequence is shown in sequence No. 2 in the Sequence Listing.

The amino acid sequence includes all of partial amino acid sequences determined by Example 2, 1 (3) and shown in Table 2, thus, the determined nucleotide sequence of insertion cDNA surely encoding for subunit b of factor G.

The recombinant DNA vector containing cDNA encoding for the polypeptide obtained by Example 2 was transfected into reproducible host microorganisms, suitable animal cells, insect or cells thereof. They were screened using a marker of vector and (1→3)-β-D-glucan binding ability as indicators. The polypeptide of the present invention can be obtained by culturing or breeding of microorganisms, animal cells, insect or cells thereof having the recombinant DNA vector.

Industrial Applicability

In the present invention, subunit a of factor G of amebocyte lysate of horseshoe crab was isolated and purified, and the amino acid sequence and cDNA nucleotide sequence encoding for said amino acid sequence were determined.

The resultant sequence included a sequence of (1→3)-β-D-glucan binding region, and polypeptide corresponding to the binding region can be obtained by gene technological methods using the cDNA. The obtained polypeptide exhibits the following various effects.

(1) Recent increase of immunodisorder patients and aged populations markedly increased patients with opportunistic infections with secondary pathogens such as Candida and Aspergillus which generally have weak pathogenicity. However, their clinical diagnosis, particularly deep-seated mycoses of organs, was difficult without invasive procedure except special patterns of diseases and often definitely diagnosed by post-autopsy (Encyclopedia of Microbiology, Gihodo Shuppan Co., Ltd., 1989).

The diagnosis of deep-seated mycoses can be carried out by measuring (1→3)-β-D-glucan with ligand-receptor assay method using labeled polypeptide contained the (1→3)-β-D-glucan binding region or (1→3)-β-D-glucan labeled with radioactive isotopes, enzymes, fluorescent or luminous compounds. Said polypeptide may be immobilized on a solid phase such as microplate, test tube or beads for the specific detection of (1→3)-β-D-glucan. These measuring methods specifically measure (1→3)-β-D-glucan derived from fungi in the body fluid for simple and rapid diagnosis of deep-seated mycoses.

(2) Medicines composed of an antifungal agent - conjugated polypeptide having a binding region with (1→3)-β-D-glucan exhibit potent affinity with lesions, and it will be new selective antifungal agents which specifically kill fungi which have (1→3)-β-D-glucan on their cell walls exist in lesion.

(3) Furthermore, recent advances of gene manipulation technology often use yeasts as hosts of vector containing gene encoding for the aimed protein in its expression. This is because the production of glycoprotein is possible and mass culture is possible as well as bacteria. However, very small amount of residues of yeast having as a component often accompanies in the products, and its measurement and removal are required. An affinity chromatography with an affinity carrier of polypeptide contained (1→3)-β-D-glucan binding region bound to support may specifically remove or determine the residue of yeasts. In addition, confirmation of the absence of yeast cell component in the product after removal was performed by the measurement using polypeptide contained (1→3)-β-D-glucan binding site as described in (1) and provided more simple and specific confirmation than that of limulus amebocyte lysate.

We claim:

1. An isolated polypeptide having an amino acid sequence defined by amino acid residue numbers 1–654 in SEQ ID No. 2.

2. An isolated polypeptide having an amino acid sequence defined by amino acid residue numbers 4–236 in SEQ ID No. 2.

3. An isolated polypeptide having an amino acid sequence defined by amino acid residue numbers 247–387 in SEQ ID No. 2.

4. An isolated polypeptide having an amino acid sequence defined by amino acid residue numbers 391–654 in SEQ ID No. 2.

* * * * *